United States Patent
Scholz et al.

(10) Patent No.: US 10,962,158 B2
(45) Date of Patent: Mar. 30, 2021

(54) CONNECTION SYSTEM

(71) Applicant: Sartorius Stedim Biotech GmbH, Göttingen (DE)

(72) Inventors: Jochen Scholz, Göttingen (DE); Sebastian Purmann, Göttingen (DE); Michael Bates, Gloucestershire (GB)

(73) Assignee: SARTORIUS STEDIM BIOTECH GMBH, Deutschland (DE)

( * ) Notice: Subject to any disclaimer, the term of this patent is extended or adjusted under 35 U.S.C. 154(b) by 420 days.

(21) Appl. No.: 15/740,890

(22) PCT Filed: Jun. 29, 2016

(86) PCT No.: PCT/EP2016/065182
§ 371 (c)(1),
(2) Date: Dec. 29, 2017

(87) PCT Pub. No.: WO2017/001504
PCT Pub. Date: Jan. 5, 2017

(65) Prior Publication Data
US 2018/0187811 A1  Jul. 5, 2018

(30) Foreign Application Priority Data
Jun. 29, 2015 (DE) .................... 20 2015 103 406.7

(51) Int. Cl.
*F16L 37/12* (2006.01)
*G01L 19/00* (2006.01)
(Continued)

(52) U.S. Cl.
CPC ......... *F16L 37/1225* (2013.01); *A61M 39/02* (2013.01); *F16L 23/04* (2013.01);
(Continued)

(58) Field of Classification Search
CPC ............... G01L 19/0046; G01L 19/144; F16L 37/1225; F16L 2201/44
(Continued)

(56) References Cited

U.S. PATENT DOCUMENTS 823,346 A * 6/1906 Maxwell .................. F16L 37/26
                                                                    285/325
8,316,706 B2   11/2012 Glocker
(Continued)

FOREIGN PATENT DOCUMENTS

DE         10302620 A1 *  8/2004  ......... G01L 19/0046
DE    102008015322 A1     9/2009
(Continued)

OTHER PUBLICATIONS

International Search Report dated Oct. 12, 2016 by the International Searching Authority for International Application No. PCT/EP2016/065182, filed on Jun. 29, 2016 and published as WO/2017/001504 on Jan. 5, 2017(Applicant—Sartorius Stedim Biotech GmbH)(Original—4 Pages/ Translated—3 pages).
(Continued)

*Primary Examiner* — David Bochna
(74) *Attorney, Agent, or Firm* — Ballard Spahr LLP

(57) ABSTRACT

Disclosed is a connection system for releasably coupling a first body (5) with a flange (25) to a fluid-conducting system in a force-fitting manner, and the invention also relates to a connection system for releasably coupling the interior of a first fluid-conducting body (5) to the interior of a second fluid-conducting body (3) in a force-fitting manner. The second body (3) has a second end with a circumferential wall (22), a membrane contact portion (9) which can be found on the wall, and an opening (43). A retaining element (2) has a passage (35) and a peripheral outer edge (24). One side and/or the passage (35) of the retaining element (2) is
(Continued)

coupled to the membrane (1), and an annular wall (26) is arranged on the same side, said annular wall being connected to the circumferential wall (22) of the second body (3). The other side is designed to contact the surface of the flange (25) of the first body (5). The retaining element (2) can also be integrated into the second body (3) when the first body (5) is fluid-conductive. The releasable connection element (4) is designed to at least partly surround the peripheral outer edge (24) of the retaining element (2) and the flange (25) of the first body (5).

18 Claims, 19 Drawing Sheets

(51) Int. Cl.
*G01L 19/14* (2006.01)
*F16L 37/20* (2006.01)
*A61M 39/02* (2006.01)
*F16L 37/252* (2006.01)
*F16L 23/04* (2006.01)
*A61M 39/10* (2006.01)

(52) U.S. Cl.
CPC ............ *F16L 37/20* (2013.01); *F16L 37/252* (2013.01); *G01L 19/0046* (2013.01); *G01L 19/144* (2013.01); *A61M 39/1011* (2013.01); *A61M 2039/1027* (2013.01); *A61M 2205/3327* (2013.01); *A61M 2205/3331* (2013.01); *F16L 2201/44* (2013.01)

(58) Field of Classification Search
USPC .......................................................... 285/3
See application file for complete search history.

(56) References Cited

U.S. PATENT DOCUMENTS

| | | | |
|---|---|---|---|
| 9,668,939 B2* | 6/2017 | Carrel | A61J 7/0472 |
| 2003/0030272 A1 | 2/2003 | Johnson et al. | |
| 2004/0168530 A1 | 9/2004 | Adolfs et al. | |
| 2009/0050213 A1 | 2/2009 | Biddell et al. | |
| 2009/0236805 A1* | 9/2009 | Dupont | G01L 19/0046 277/609 |
| 2011/0011176 A1 | 1/2011 | Glocker | |
| 2012/0240686 A1 | 9/2012 | Blomberg et al. | |
| 2013/0014588 A1* | 1/2013 | Feldmeier | G01L 19/0023 73/756 |
| 2014/0210202 A1* | 7/2014 | Hess | F16L 37/1225 285/81 |
| 2020/0080675 A1* | 3/2020 | White | F16L 37/084 |

FOREIGN PATENT DOCUMENTS

| | | | | |
|---|---|---|---|---|
| EP | 0208955 A2 * | 1/1987 | | G01L 19/003 |
| EP | 0631080 A1 | 12/1994 | | |
| EP | 1775510 B1 | 2/2010 | | |
| EP | 2252202 A1 | 11/2010 | | |
| EP | 2142835 B1 | 8/2011 | | |
| EP | 2727654 A1 * | 5/2014 | | F16L 37/1225 |
| EP | 3260834 A1 * | 12/2017 | | G01L 19/0007 |
| EP | 3309528 A1 * | 4/2018 | | G01F 23/00 |
| WO | WO-01/44707 A1 | 6/2001 | | |
| WO | WO-2006/117138 A1 | 11/2006 | | |
| WO | WO-2007/063390 A1 | 6/2007 | | |
| WO | WO-2017/001504 A1 | 9/2009 | | |

OTHER PUBLICATIONS

Written Opinion dated Oct. 12, 2016 by the International Searching Authority for International Application No. PCT/EP2016/065182, filed on Jun. 29, 2016 and published as WO/2017/001504 on Jan. 5, 2017(Applicant—Sartorius Stedim Biotech GmbH) (Original—7 Pages/ Translated—7 pages).

* cited by examiner

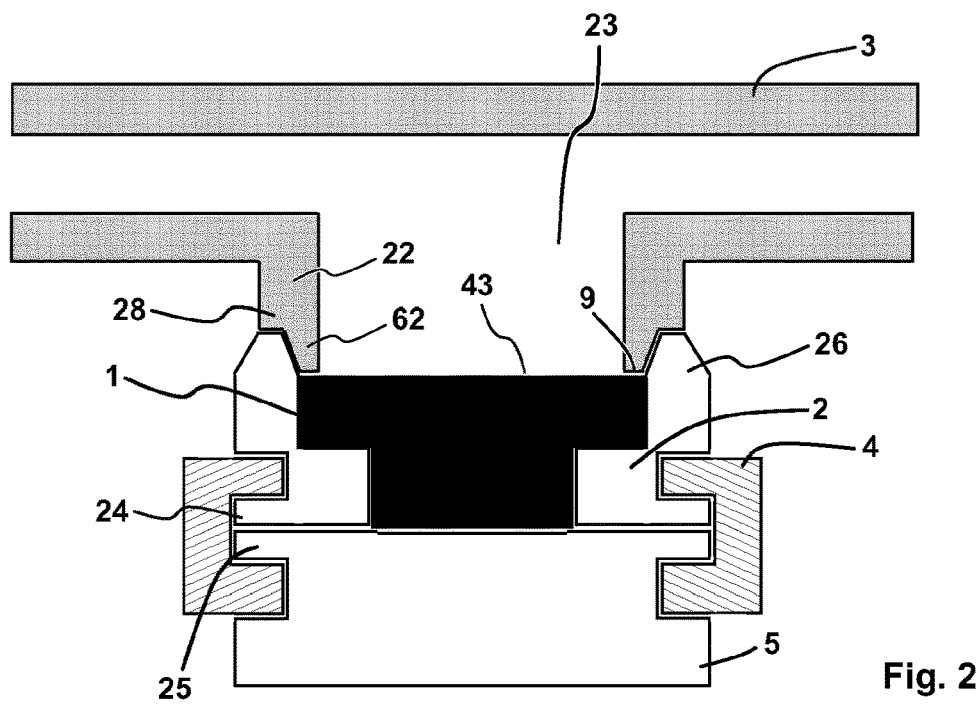
Fig. 2
Fig. 3
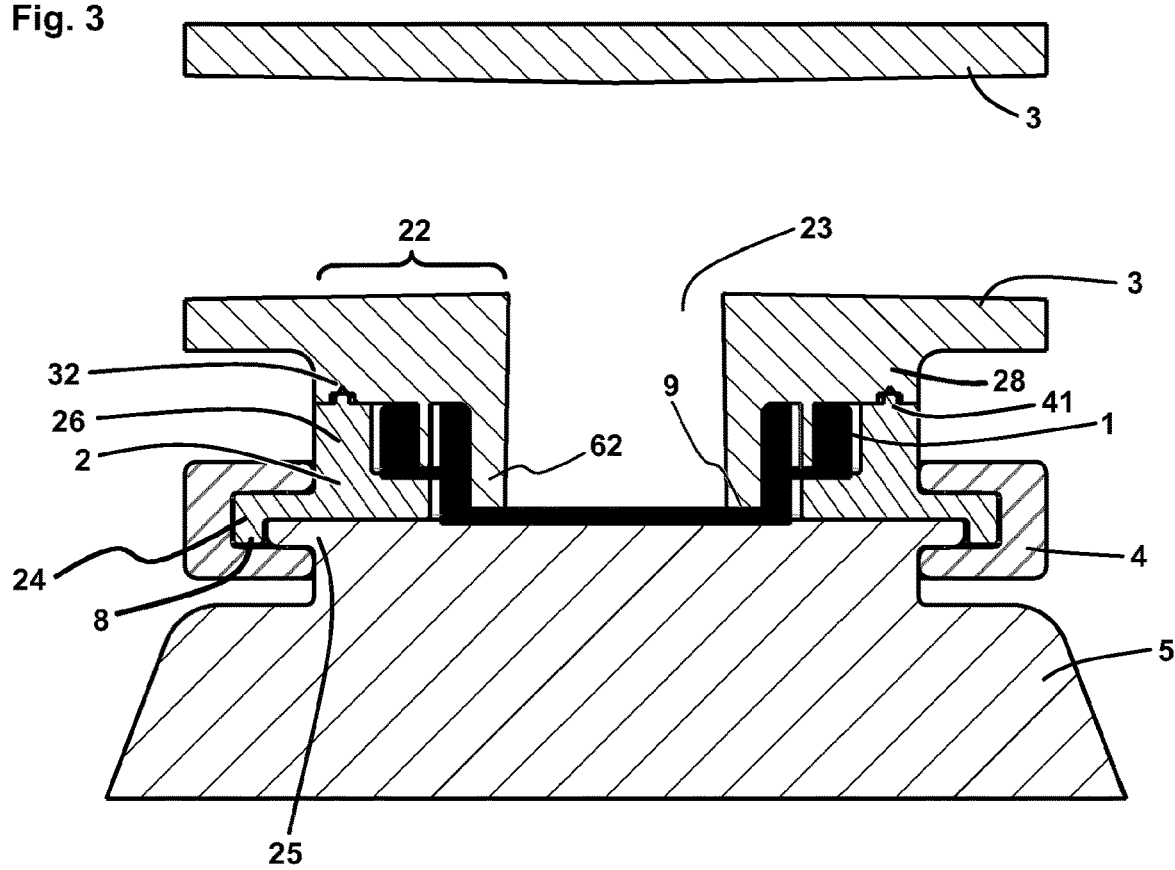

Fig. 11A
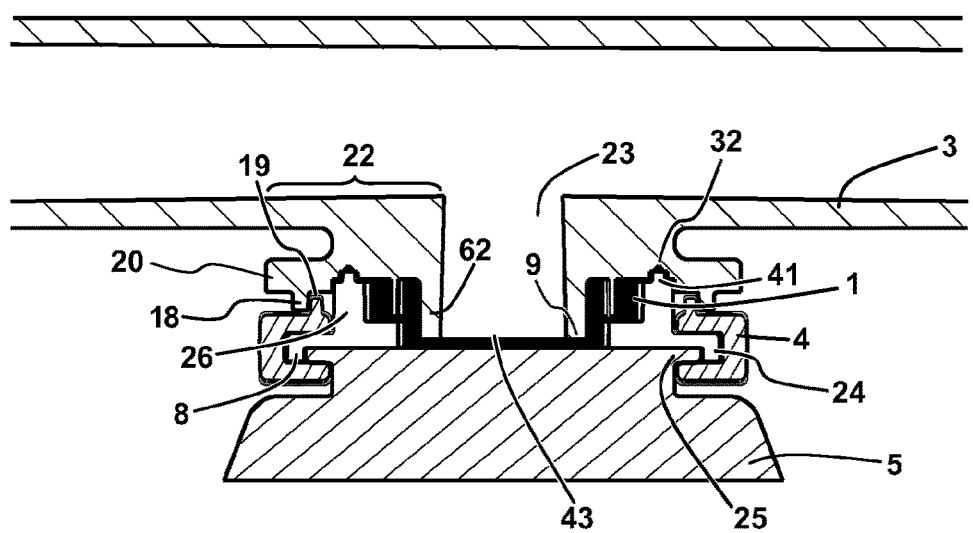
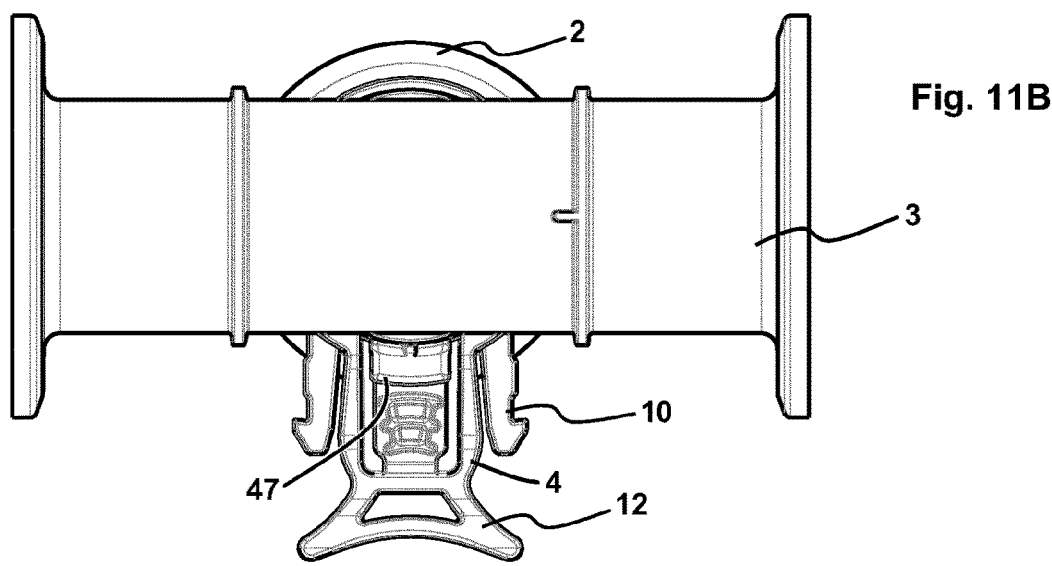
Fig. 11B
Fig. 11C
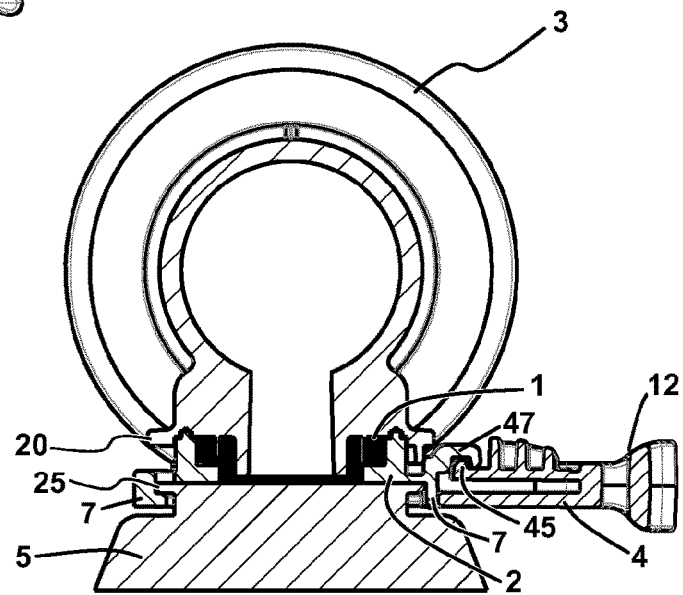

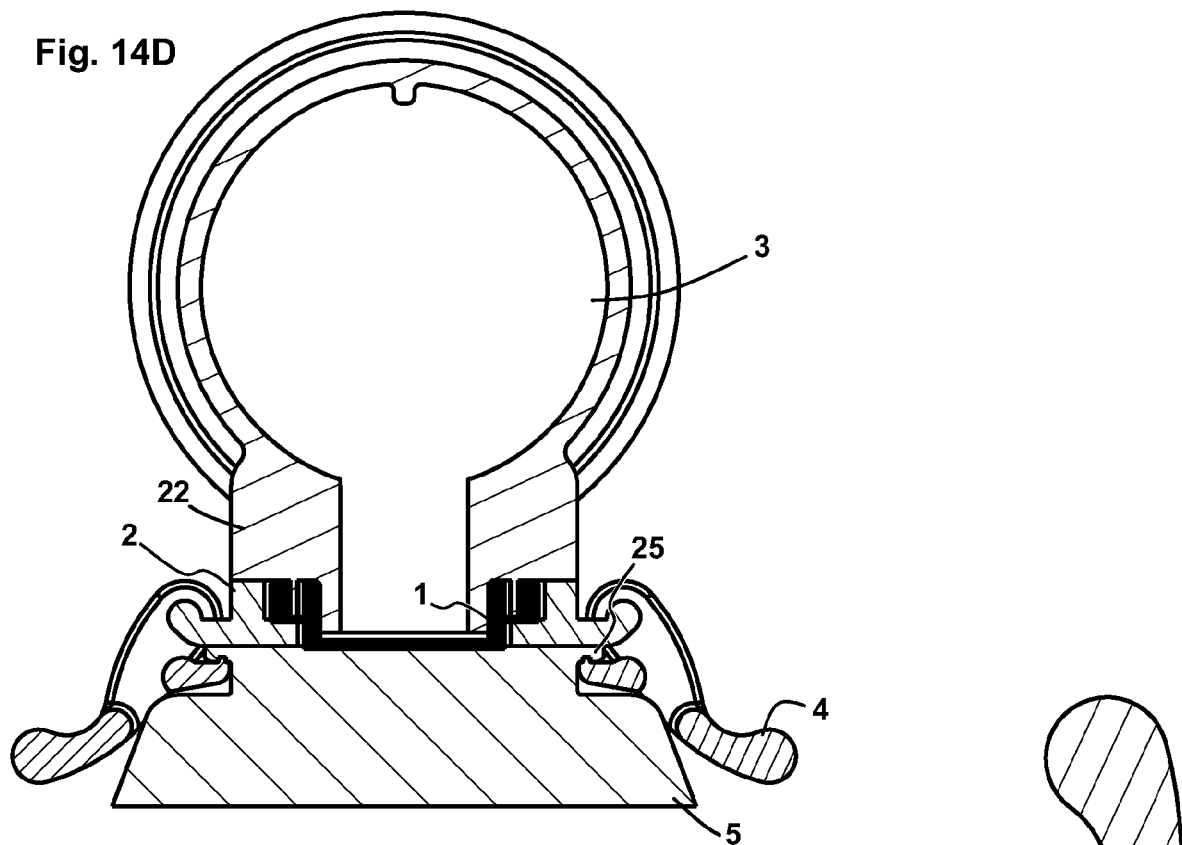
Fig. 14D
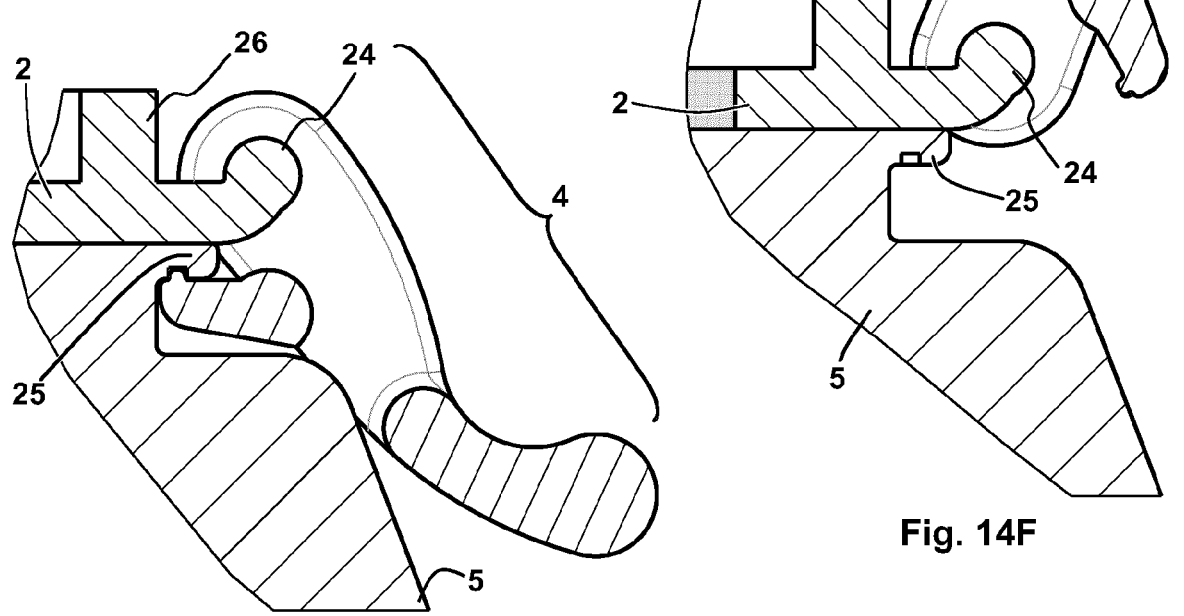
Fig. 14E
Fig. 14F

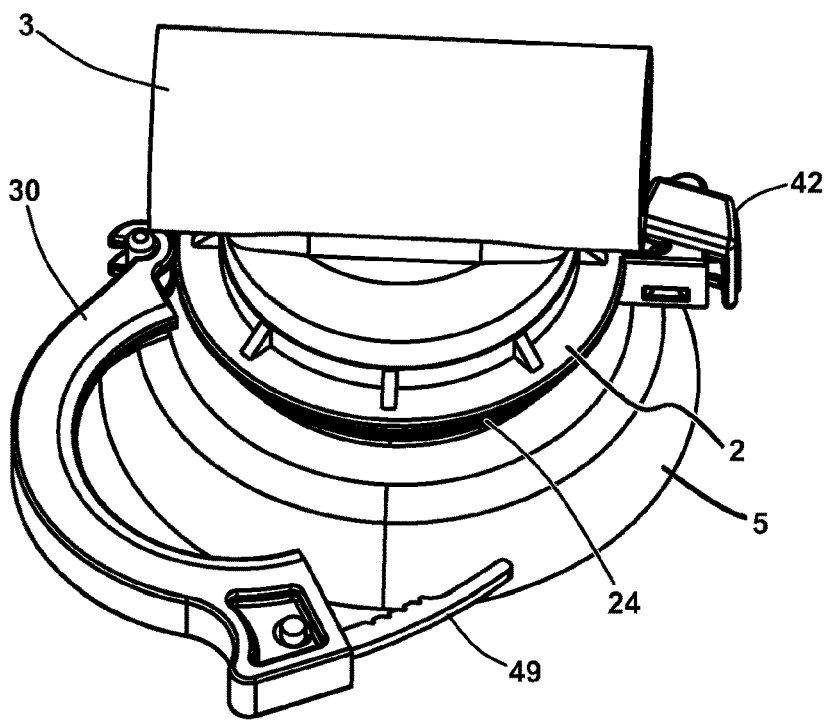
Fig. 16C
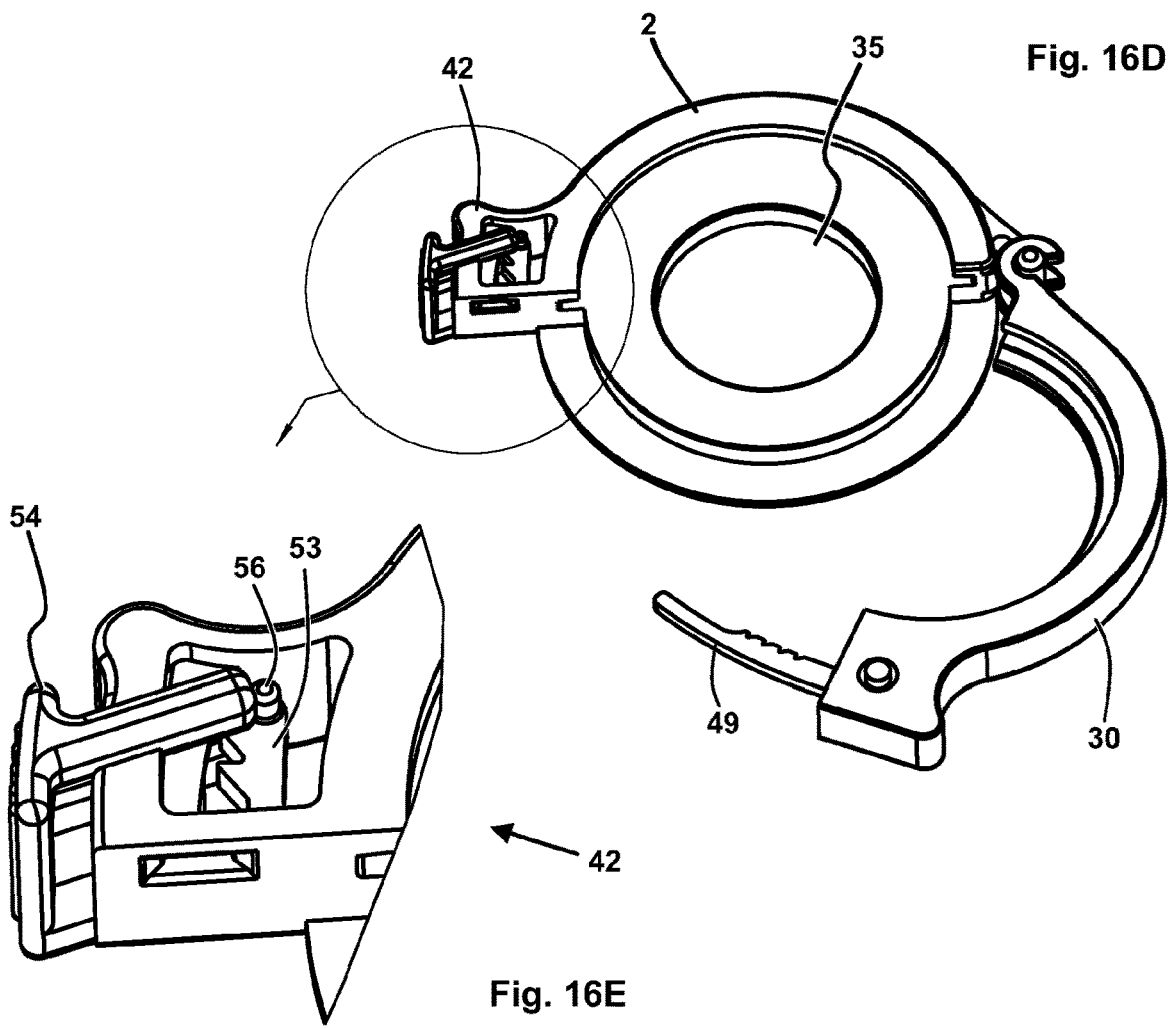
Fig. 16D
Fig. 16E

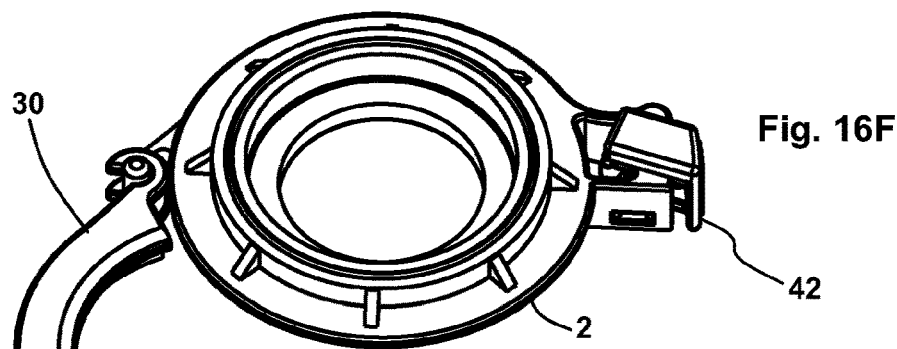
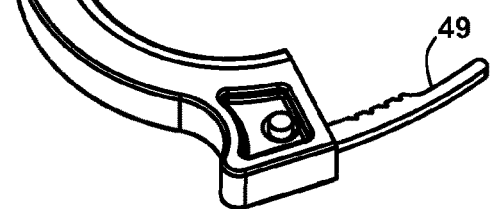
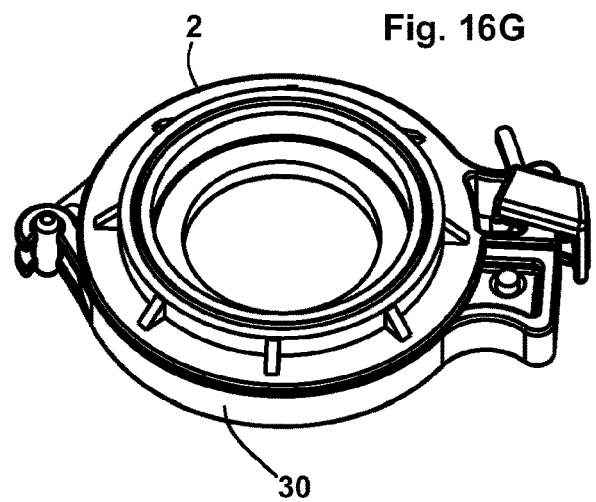
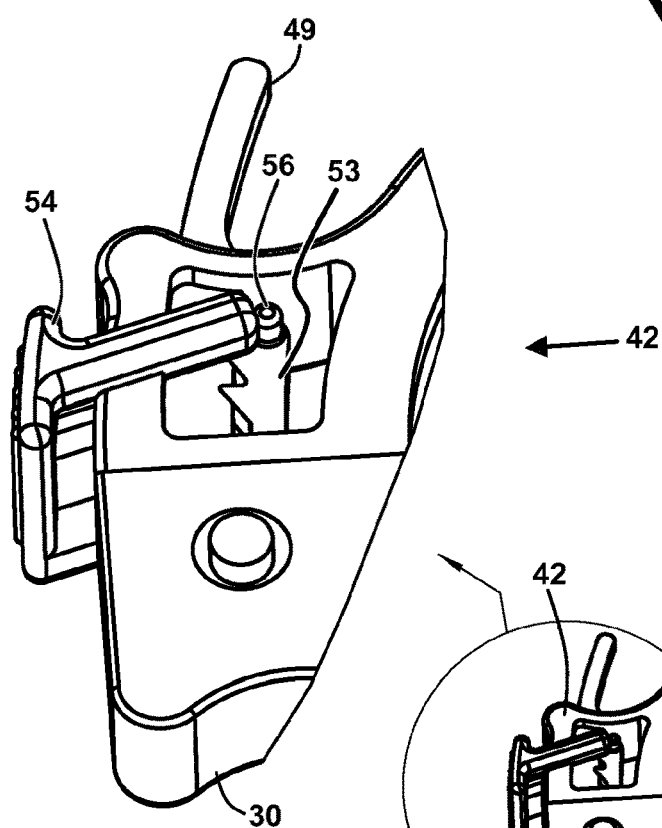
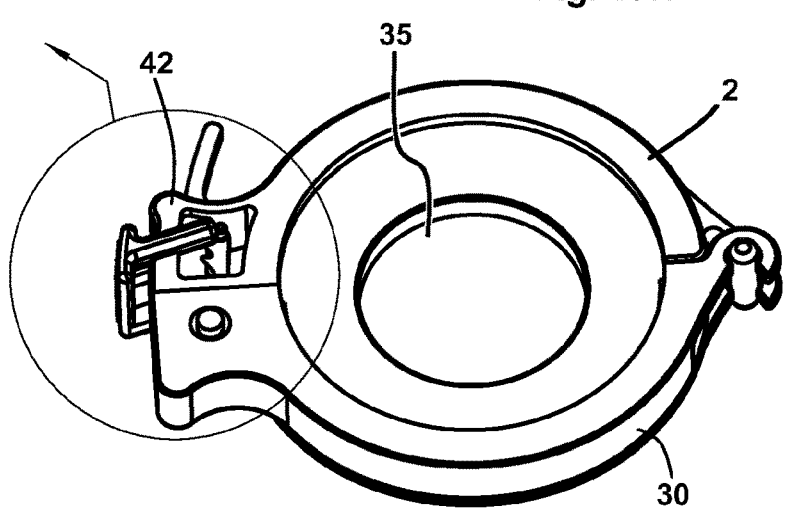

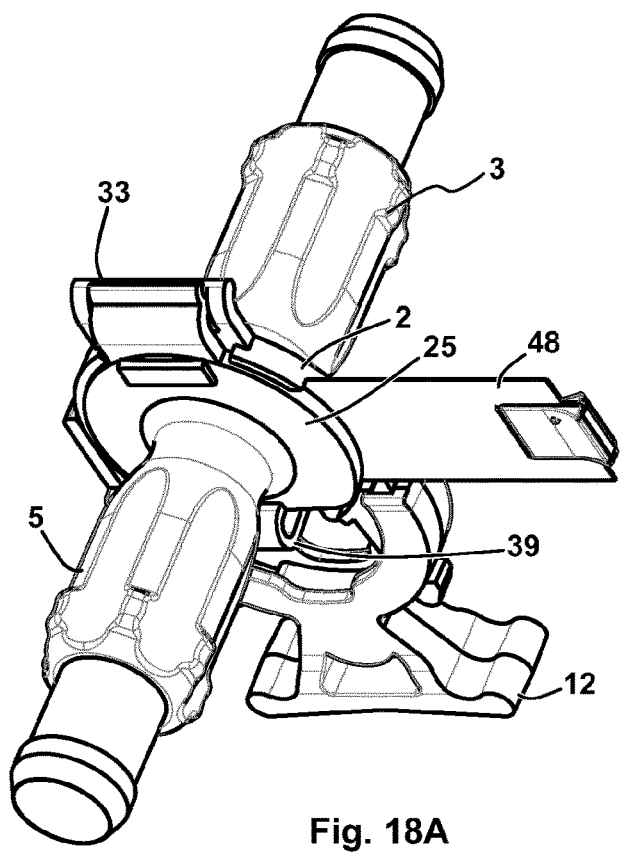
Fig. 18A
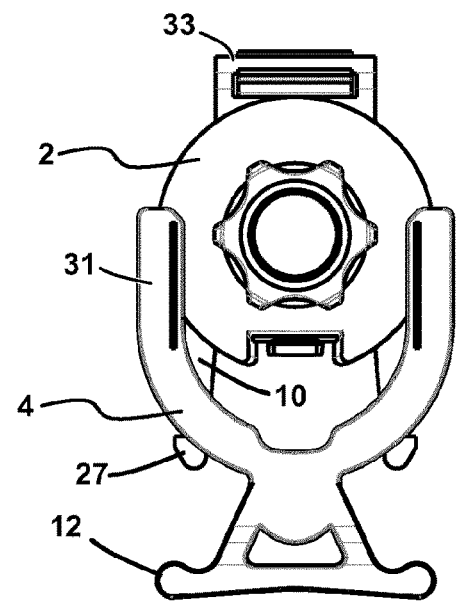
Fig. 18C
Fig. 18B
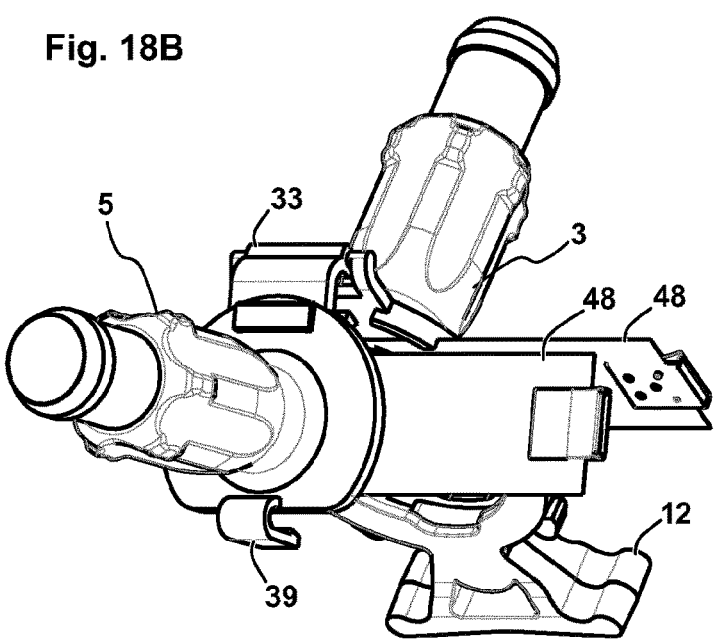
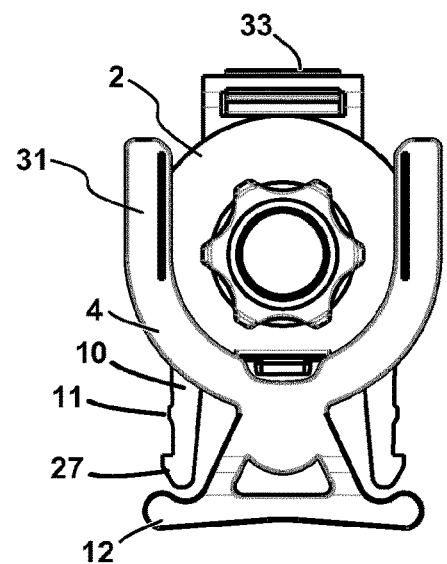
Fig. 18D

CONNECTION SYSTEM

CROSS-REFERENCE TO RELATED APPLICATIONS

This is a U.S. National Phase Application of International Application No. PCT/EP2016/065182, filed Jun. 29, 2016, which claims the benefit of and the priority to German utility model DE 20 2015 103 406, filed on 29 Jun. 2015, which is hereby incorporated herein by reference in its entirety.

TECHNICAL FIELD

The present disclosure relates to a connection system, in particular a connection system for releasably force-fittingly coupling a body with a fluid-carrying system via a membrane, or for releasably force-fittingly coupling two fluid-carrying bodies. In some embodiments, the connection system serves in coupling a pressure sensor and a pressure transducer. Disclosed is also a method, in which the connection system is used.

BACKGROUND

The following discussion of the background of the disclosure is merely provided to aid the reader in understanding the same, and is not admitted to describe or constitute prior art.

For biotechnological production processes, sterile and aseptic connections between reaction vessels and gadgets, analyzers etc. are of high importance. Since processes need to be carried out under aseptic conditions, sterile connections and lines have to be provided in such a way that no contamination by environmental factors can occur both during operation and during the preceding connection. As an example, single-use plastic bags with flexible thermoplastic lines require connections which ensure that both the bags and the lines remain sterile.

Pressure sensors are used in a variety of technical flow processes for monitoring and control purposes. With the spread of single-use devices in the biopharmaceutical industry, the use of single-use sensors for pressure measurement is also gaining increasing importance. Important application areas include inter alia cross-flow or filtration applications. European Patent EP 2 252 202 discloses a connection member suitable for a single-use pressure transducer. The corresponding system element serves as a releasable, sealed connection of a measuring element to a fluid system. The pressure transducer, being a sealed flow-through part of the fluid system, transmits the pressure forces via a membrane to a measuring element that includes e.g. a piezo force gauge.

Single-use pressure sensors are typically made of plastic, while the respective measuring head usually contains metal such as e.g. stainless steel. The connection of a single-use pressure sensor with a fixed metal measuring head of metal must both be easy to carry out and ensure a firm and defined compression to each other.

For this purpose, auxiliary devices or aids such as e.g. a hood and locking pins are usually provided to achieve the required measuring accuracy and reproducibility. However, these auxiliary devices are generally complex to handle and bear the risk of errors by the user. This can lead to inaccurate measurements. Furthermore, the time required for installation and deinstallation is high.

SUMMARY

In typical embodiments, a connection disclosed herein provides a robust and defined mechanical coupling of a single-use component to a reusable body such as a measuring element, with ease of mounting. In some embodiments, mounting can be carried out safely and reliably even with a single hand. A connection disclosed herein typically also offers a robust and defined mechanical coupling of two single-use components to each other.

According to a first aspect, there is disclosed a connection system for releasably force-fittingly coupling a first body to a fluid-carrying system via a fluid-tight membrane. A respective fluid may be a gas or a liquid. The connection system includes the fluid-tight membrane. The connection system also includes a second body. The second body includes an interior space which is coupled to the fluid-carrying system. Typically, the second body is connected to the fluid carrying system. In this case, the interior space of the second body is generally filled with the fluid of the fluid-carrying system. The second body also includes a port. The port is in communication with the interior space of the second body. This port may for example be an outlet, including an opening. This port is generally a port of the interior space of the second body. The interior space of the second body typically opens out into an opening. In addition, the connection system includes a disc-shaped holding member, which may also be an integral part of the second body in the form of a flange-like end. In this case, the second end of the second body defines a flange-like disc-shaped holding member with a peripheral outer edge. The peripheral outer edge is facing away from the interior space of the second body. Furthermore, the connection system also includes a releasable connection member.

The connection system according to the first aspect is designed to allow a force-fitting coupling with a first body. Such a first body includes a first end with a flange. The second body includes a second end with an interior space and a circumferential wall. As already indicated above, in some embodiments the connection system includes a disc-shaped holding member, while in some embodiments the second body ends in a flange-like, disc-shaped holding member. In embodiments where the disc-shaped holding member defines a separate component, it includes a passage. Such a distinct disc-shaped holding member includes a first side, a second side and a peripheral outer edge. The first side and/or the passage of the disc-shaped holding member is or are, respectively, coupled to the membrane. As an example, the first side and/or the passage of the disc-shaped holding member may be connected to the membrane. In embodiments where the disc-shaped holding member defines a distinct component, the first side of the disc-shaped holding member is furthermore typically in contact with the second end of the second body. The second side of the holding member is generally designed for a surface-to-surface contact with the flange of the first body, for example, to be seated on the flange. It may be designed to be connected to the flange of the first body. Also in embodiments where the flange-like, disc-shaped holding member defines the second end of the second body, the holding member generally includes a side which is designed for a surface-to-surface contact with the flange of the first body, for example for resting on the flange and/or to be connected surface-to-surface to the flange of the first body. In embodiments where the flange-like, disc-shaped holding member defines the second end of the second body, the flange-like, disc-shaped holding member generally is in contact with the membrane.

In a mounted state, the first body is coupled to the second body, and fixed to the second body by locking it in place. The membrane is generally at least partly arranged between the second end, which is defined by the second body, and the first end, which is defined by the first body. In embodiments where a disc-shaped holding member defines a distinct component, also this disc-shaped holding member is arranged between the second end, which is defined by the second body, and the first end, which is defined by the first body. Such a first body includes a first end with a flange. In embodiments where a flange-like, disc-shaped holding member defines the second end of the second body, the geometry of this second end is generally matched to the geometry of the first end. In some embodiments, the geometry of this second end is matched to the geometry of the first end to such an extent that a fluid-tight coupling is possible. Also, in some embodiments where a disc-shaped holding member defines a distinct component, the geometry of the second end may be matched to the geometry of the first end.

In some embodiments, for example in embodiments where the second end of the second body defines a flange-like disk-shaped holding member, the first body typically includes an interior space. In a connection system disclosed herein, e.g. in a system in which the second end of the second body defines a flange-like disc-shaped holding member, the first body may also be fluid-carrying. In some embodiments, for example in embodiments where the second end of the second body defines a flange-like, disc-shaped holding member, the first body typically contains an interior space and is fluid-carrying. In some embodiments, the first body contains an interior space, however, it is not fluid-carrying. For example, in embodiments where the disc-shaped holding member defines a distinct component, the first body may include an interior space, however, it may not be fluid-carrying. In some embodiments, the disc-shaped holding member defines a separate component and the first body does not include an interior space.

As already indicated above, the connection system furthermore contains a releasable connection member. The releasable connection member is designed to at least partially circumferentially grip around the peripheral outer edge of the disc-shaped holding member, or of the flange-like disc-shaped holding member, respectively, and around the flange of the first body. In this way, the disc-shaped holding member can be force-fittingly fixed on the first body by means of the connection member.

In typical embodiments, the circumferential wall of the second body includes a circumferential membrane contact portion around the port, e.g. the opening, which is in contact with the membrane or is connected to the membrane. The circumferential membrane contact portion is generally oriented in such a way that it faces the first body. In some embodiments, the circumferential membrane contact portion may entirely define the side of the circumferential wall facing the flange of the first body. In such embodiments, the entire side of the circumferential wall facing the flange of the first body typically is in contact with the membrane or is coupled to the same. Essentially the entire side of the circumferential wall facing the flange of the first body may also be in contact with the membrane. As an example, essentially the entire side of the circumferential wall facing the flange of the first body may be in contact with the membrane, or the entire side of the circumferential wall facing the flange of the first body may be in complete contact with the membrane. In some embodiments, the circumferential membrane contact portion does not entirely define the side of the peripheral wall facing the flange of the first body. In such embodiments, this side of the circumferential wall includes a further wall portion. For example, in embodiments where the second body ends in a flange-like disc-shaped holding member, the flange-like, disc-shaped holding member may contain the membrane contact portion, being circumferential around the port, as well as a further portion that does not contact the membrane. This further portion, which does not contact the membrane, in some embodiments abuts the membrane contact portion. In some embodiments, this further portion does not abut the membrane contact portion. In embodiments where, in addition to the membrane contact portion, a further wall portion of the circumferential wall faces the flange of the first body, generally only a portion of the side of the circumferential wall facing the flange of the first body is in contact with the membrane.

In some embodiments, where there is a disc-shaped retaining member defining a distinct component, the second body furthermore includes a recess as a retrace, circumferential around the circumferential wall. In some embodiments, where the disc-shaped holding member defines a flange-like end of the second body, a recess as a retrace is arranged on the circumferential wall.

In some embodiments where a separate holding member is present as a distinct component, a circumferential wall is arranged on the first side of the disc-shaped holding member, which is connected to the circumferential wall of the second body. In typical embodiments the circumferential wall on the first side of the disc-shaped holding member and the peripheral wall of the second body include geometries that allow a circumferential contact of the two walls. As an example, the circumferential wall of the disc-shaped holding member may include a surface area that essentially is in complete circumferential contact with the circumferential wall of the second body. Likewise, the circumferential wall of the second body may include a surface area that essentially is in complete circumferential contact with the circumferential wall of the disc-shaped holding member. In some embodiments, the circumferential wall of the disc-shaped holding member includes a surface area that is in complete circumferential contact with the circumferential wall of the second body. In some embodiments, the circumferential wall of the second body includes a surface area that is in complete circumferential contact with the circumferential wall of the disc-shaped holding member. In some embodiments, the circumferential wall of the disc-shaped holding member includes a surface area that is essentially in circumferential contact with a surface area of the circumferential wall of the second body. In some embodiments, the circumferential wall of the disc-shaped holding member includes a surface area that is in complete circumferential contact with a surface area of the circumferential wall of the second body. In some embodiments, a circumferential surface area of the circumferential wall of the second body may be essentially completely connected to the first side of the disc-shaped holding member. A circumferential surface area of the circumferential wall of the second body may also be completely connected to the first side of the disc-shaped holding member. In some embodiments, a circumferential surface area of the circumferential wall on the first side of the disc-shaped holding member may be essentially completely connected to the second body. In some embodiments, a circumferential surface area of the circumferential wall on the first side of the disc-shaped holding member is completely connected to the second body. Also, a circumferential surface area of the circumferential wall of the second body may be essentially completely connected to the disc-shaped holding member. In some embodiments, a circumferential surface area of the circumferential wall of the second body is completely connected to the disc-shaped holding member.

The side of the flange of the first body with which the second side of the holding member, or the flange-shaped, disc-shaped holding member integrated in the second body, can be connected surface-to-surface, defines a plane. Accordingly, this plane is parallel to a plane defined by the holding member. In some embodiments, the planes of the flange and of the holding member are essentially perpendicular to an axis that is defined by the circumferential wall of the second body that surrounds the interior space, e.g. the cylinder interior of the second body.

In a connection system according to the first aspect, the membrane is typically arranged between the circumferential wall of the second body and the disc-shaped holding member. Generally, the fluid-tight membrane is in surface-to-surface contact with the circumferential wall of the second body in the area of the membrane contact portion. The fluid-tight membrane may rest on the circumferential wall of the second body in the area of a circumferential membrane contact portion.

In some embodiments of the connection system according to the first aspect, the disk-shaped holding member and the connection member lockably engage each other. In some of these embodiments, the connection system may exist in an open and a closed state if it includes the first body. In an open state, the releasable connection member is coupled to the disc-shaped holding member, typically moveably coupled. The releasable connection member may, for example, be slidable or twistable in relation to the disc-shaped holding member. In such an open state, the first body is coupled to the disc-shaped holding member and/or the membrane. The first body may also be releasably connected to the disc-shaped holding member and/or the membrane. In a closed state, the disc-shaped holding member and the connection member are locked in place, so that the connection member and the disc-shaped holding member are force-fittingly connected to each other. In a closed state, the disc-shaped holding member and the connection member are generally releasably connected to each other. In this state, the connection member is no longer movable relative to the disc-shaped holding member.

As already explained above, in some embodiments the connection system according to the first aspect also includes the first body. In such a case, the second side of the holding member is typically in surface-to-surface contact with the flange of the first body. The second side of the holding member may for instance be seated on the flange of the first body. In such embodiments, the releasable connection member in its locked state at least partially grips around the peripheral outer edge of the holding member and the flange of the first body.

In some embodiments of the connection system according to the first aspect, on the circumferential wall of the second body there is arranged a circumferential bead. The circumferential bead may for example be arranged at the membrane contact portion. In some embodiments, in which a circumferential bead is present, the remaining part of the circumferential wall may be regarded as a recess as a retrace around the circumferential wall. In such embodiments, the fluid-tight membrane may contact the circumferential bead, it may for example be connected to the circumferential bead. The fluid-tight membrane in some embodiments rests on the circumferential wall of the second body. In some embodiments, the membrane is arranged between the circumferential bead and the holding member. In some embodiments, the circumferential wall of the holding member is connected to the recess as a retrace of the second body.

In some embodiments of the connection system according to the first aspect, the first body includes a first cylindrical end with a flange. In some embodiments, the second body includes a second cylindrical end with the cylinder interior and a circumferential wall. The circumferential wall may in some embodiments be circularly circumferential. In some embodiments, the first body includes a first cylindrical end and the second body includes a second cylindrical end with a cylinder interior.

As already indicated above, the connection system includes a disc-shaped holding member, which in some embodiments is an distinct component. The disc-shaped holding member includes a passage such as an opening. In some embodiments, the passage is a round opening, such as a circular opening or an oval opening. In some embodiments, on the first side of the disc-shaped holding member there is arranged a ring-shaped wall. The annular wall may, in some embodiments, be uniformly spaced from the passage of the disk-shaped holding member.

In embodiments where a circumferential bead is arranged on the circumferential wall of the second body, it may be a ring bead, for example. A circumferential bead on the circumferential wall of the second body defines in some embodiments an edge of the interior space of the second body. Typically, a circumferential wall of such a circumferential bead includes one or more portions which is/are in contact with the membrane. In some embodiments, the circumferential wall of a corresponding circumferential bead is essentially in complete contact with the membrane. In some embodiments, the circumferential wall of a circumferential bead is in complete contact with the membrane. In some embodiments, the membrane is arranged between such a circumferential bead and the disc-shaped holding member.

In some embodiments, in which the disc-shaped holding member defines a distinct component, there is a circumferential surface area arranged on the second side of the holding member, which is in essentially circumferential contact with the flange of the first body. In some embodiments, a circumferential surface area on the second side of the holding member is in complete contact with the flange of the first body. In some embodiments, in which the disc-shaped holding member defines the second end of the second body, there is a circumferential surface area arranged on the holding member, which is in essentially circumferential contact with the flange of the first body. In some embodiments, a circumferential surface area on the holding member is in complete contact with the flange of the first body.

The releasable connection member is in contact with both the disc-shaped holding member and the flange of the first body. The releasable connection member at least partially grips around the peripheral outer edge of the disc-shaped holding member and the flange of the first body. In some embodiments, the disc-shaped holding member includes a surface area that is at least partially in contact with a portion of the flange of the first body. In some embodiments, the disc-shaped holding member includes a surface area that is at least essentially over the entire surface area in contact with a portion of the flange of the first body. For example, the disc-shaped holding member may include a surface area that is in contact with a corresponding surface area of the flange of the first body. For example, the disc-shaped holding member may include a surface area that is seated on a corresponding surface area of the flange of the first body. In some embodiments, such a surface area is about one square millimeter to about 10 square centimeters in size. In some embodiments, such a surface area is about 50 square millimeters to about 20 square centimeters in size. In some embodiments, such a surface area is about one square millimeter to about 50 square centimeters in size. In some embodiments, such a surface area of the disc-shaped holding member is in complete contact with the entire surface area of a portion of the flange of the first body.

A surface area of the disc-shaped holding member that is at least partially in contact with a portion of the flange of the first body may have any shape. In some embodiments such a surface area may be round, e.g. circular or oval. A respective surface area may also be any polygon, such as a triangle or a pentagon. In some embodiments, a surface area of the disc-shaped holding member which at least partially is in contact with a portion of the flange of the first body, is of square or rectangular shape. Such a surface area can also be a hexagonal or higher polygonal.

The peripheral outer edge of the disk-shaped holding member may in some embodiments define a flat wall. In some embodiments, the peripheral outer edge may define a completely or partially circumferential protrusion. Such a protrusion may for example radially protrude outward parallel to the plane of the flange. Such a protrusion may also be inclined relative to the plane of the flange, for instance in the direction of the second body.

In some embodiments, the second end of the second body defines a branching of the fluid-carrying second body. The for instance cylindrical end includes the circumferential wall. A respective cylindrical end may also include the circumferential bead and a recess in the form of a retrace as described above. In some embodiments, the membrane at least partially butts against the retrace-like recess of the second body. To this end, the membrane may include a bead, as described in European Patent EP 2 252 202.

In some embodiments of the connection system of the first aspect, the second fluid-carrying body is a housing having a means for sealed fluid communication with a fluid system.

The disc-shaped holding member may in top view onto the first or the second side be of any shape. In some embodiment, the disc-shaped holding member has an oval or circular outline, when viewed from the first or the second side. In some embodiments, the outline of the disc-shaped holding member includes one or more corners, when seen from the first or the second side. The outline may, for example, be triangular, rectangular, square, pentagonal, or hexagonal. In some embodiments, the disc-shaped holding member defines a holding ring.

In plan view, also the circumferential wall of the second body may have any shape. The thickness of the circumferential wall of the second body may vary as desired. In one embodiment, the circumferential wall of the second body is of essentially uniform thickness. In one embodiment, the circumferential wall of the second body is of uniform thickness.

In some embodiments of the connection system of the first aspect, the first body is a measuring element, and the second body is a measuring chamber that is connectable to a fluid system in a manner that allows the passage of fluid through the connection. In such embodiments, the membrane is typically much more resilient than the inner wall of the interior space of the second body, and it allows the transfer of pressure forces from the measuring chamber to the measuring element. The first side and the passage of the disc-shaped holding member are in such embodiments generally connected to the membrane. The disc-shaped holding member includes a first side, a second side and a peripheral outer edge. The first side of the disc-shaped holding member is coupled to the membrane and to the circumferential wall of the measuring chamber. The second side of the disc-shaped holding member is designed for coupling to the flange of the measuring element. Typically, the second side of the disc-shaped holding member is designed to contact the flange of the measuring element. The disc-shaped holding member allows being fixed force-fittingly, i.e. in a force-locked way, to the measuring element by means of a releasable connection member. In embodiments where the connection system includes the measuring element, the second side of the disc-shaped holding member is generally coupled to the measuring element. The disc-shaped holding member is in this case force-fittingly fixed to the measuring element by means of a releasable connection member. In some embodiments, the first side of the disc-shaped holding member butts against the membrane and against the circumferential wall of the measuring chamber.

In some embodiments, the first body is a measuring element and the second body is a measuring chamber that includes a circumferential wall with a recess, and that is connectable to a fluid system in a manner that allows fluid to pass. The recess has an edge which is in surface-to-surface contact with the liquid-tight membrane. As an example, a liquid-tight membrane may be seated on such an edge. The membrane is much more flexible than the walls of the measuring chamber. The membrane generally allows a transfer of compressive forces from the measuring chamber to the measuring element. The membrane is sandwiched between the edge of the measuring chamber and a disk-shaped holding member in the form of a holding ring. The holding ring includes a first side, a second side and a peripheral outer edge. The first side is coupled to the membrane and to the wall of the measuring chamber. In some embodiments, the first side is connected to the membrane and the wall of the measuring chamber. The second side of the holding ring is coupled to the measuring element. The holding ring is force-fittingly fixed to the measuring element by means of a releasable connection member. In some embodiments of the connection system of the first aspect, the second side of the holding ring is in surface-to-surface contact with the measuring element. In some embodiments, the second side of the holding ring abuts the transducer. In some embodiments, the connection member at least partially grips around the peripheral outer edge of the holding ring. In some embodiments, the measuring element has a flange. The connection member in such embodiments at least partially grips around the flange.

In some embodiments of the connection system of the first aspect, the releasable connection member grips around one or more portions of the peripheral outer edge of the disk-shaped holding member. In these embodiments, the releasable connection member generally grips around one or more corresponding adjacent portions of the flange of the first body. As an example, the peripheral outer edge of the disc-shaped holding member may have a circumference, and one or more portions of the releasable connection member may grip around a certain portion thereof, such as about 75% or about 25%.

The passage of the disk-shaped holding member typically establishes a connection between the interior of the second body and the membrane. The passage of the disk-shaped holding member is typically an opening. In some embodiments, the passage may consist of a plurality of openings. A corresponding opening may be of any shape and size as long as the desired function of the arrangement of the body and/or the membrane of the selected shape is achieved. The maximum size of the passage is then defined by the dimensions of the interior space of the second body. In some embodiments, a respective opening has a round shape, such as elliptical or circular. In some embodiments, such an opening has a triangular, rectangular, square, pentagonal, hexagonal or higher polyangular shape. The shape of such a passage, e. g. an opening, may be selected independently of the shape of other components of the disc-shaped holding member as well as independently of the shape of the outline of the disc-shaped holding member.

In typical embodiments of the connection system according to the first aspect, the circumferential wall arranged on the first side of the disc-shaped holding member is essentially uniformly spaced to the central passage.

As already indicated above, the disc-shaped holding member defines a plane. This plane is typically parallel to a plane defined by the membrane. In some embodiments, the second side of the disc-shaped holding member, which is designed for a surface-to-surface contact with the flange of the first body, or which is seated on the flange of the first body, is at least essentially planar.

In typical embodiments, the membrane is permanently connected to the circumferential wall of the second body and the disc-shaped holding member. In some embodiments, the membrane is welded, glued or sealed to the surrounding wall of the second body and to the disc-shaped holding member, or clamped to the surrounding wall. The membrane may also be connected to the peripheral wall of the second body and to the disc-shaped holding member by means of multi-component injection moulding and/or liquid silicone rubber, also known by its abbreviation LSR. In some embodiments, the membrane may be connected to the peripheral wall of the second body and/or the disc-shaped holding member by a combination of several of the means named above.

In some embodiments, the disk-shaped holding member is welded, glued or sealed to the peripheral wall of the second body. The disk-shaped holding member may also be clamped to the circumferential wall of the second body, or be connected to the peripheral wall of the second body by multi-component injection moulding and/or liquid silicone rubber. The disc-shaped holding member may also be connected to the peripheral wall of the second body by a combination of several of the means named above.

According to a second aspect, there is provided a connection system for releasably force-fittingly coupling the interior space of a first fluid-carrying body to the interior space of a second fluid-carrying body. The connection system may be a system for releasably sealingly coupling the interior space of the first fluid-carrying body to the interior space of a second fluid-carrying body. The first body includes a first cylindrical end with a flange. The second body includes a second cylindrical end that opens out into a flange-like disk-shaped holding member. The disc-shaped holding member includes a central port of the interior space of the second fluid-carrying body, for example an outlet. The disc-shaped holding member includes a first side, a second side and a peripheral outer edge. On the first side of the holding member, there is arranged an annular protrusion, which is substantially uniformly spaced from the central port. The first side of the holding member is designed for surface-to-surface contact with the flange of the first body. As an example, the first side of the holding member rests on the flange of the first body. The connection system contains a connection member, which at least partially grips around the peripheral outer edge of the holding member and the flange of the first body. Thereby the disk-shaped holding member is fixed to the first body in a liquid-tight manner by means of the releasable connection member.

In some embodiments, the connection system according to the second aspect further includes a membrane. The membrane is arranged between the flange of the first body and the first side of the holding member of the second body. The membrane may, in some embodiments, be releasably arranged between the first body and the second body.

The flange-like disk-shaped holding member includes a passage or a central outlet. The passage of the flange-like disk-shaped holding member is generally an opening. In some embodiments, the passage may consist of a plurality of openings. A respective opening may be of any shape and size as long as the desired function of connecting the fluid carrying bodies is achieved. The maximal size of the passage is then defined by the dimensions of the interior space of the second body. In some embodiments, a corresponding opening has a round shape, such as elliptical or circular. In some embodiments, such an opening has a triangular, rectangular, square, pentagonal, hexagonal or higher polyangular shape. The shape of the passage or outlet of such a flange-like disc-shaped holding member, for instance an opening may be selected independently of the shape of other components of the flange-like disk-shaped holding member or of the shape of the outline of the flange-like disk-shaped holding member.

In plan view onto the first or the second side, the flange-like disk-shaped holding member may have any shape. In some embodiments, the flange-like disk-shaped holding member, when seen from the first or the second side, has an oval or circular outline. In some embodiments, the outline of the disc-shaped holding member, when seen from the first or the second side, includes one or more corners. The outline may, for example, be triangular, rectangular, square, pentagonal or hexagonal. In some embodiments, the disc-shaped holding member defines a holding ring.

The flange-like disc-shaped holding member in some embodiments includes a surface area that at least partially contacts a portion of the flange of the first body. In some embodiments, the flange-like disc-shaped holding member includes a surface area that essentially over the entire surface contacts a portion of the flange of the first body. The flange-like, disc-shaped holding member may, for example, include a surface area which is designed for surface-to-surface contact with a corresponding surface area of the flange of the first body. Such a surface area of the flange-like disk-shaped holding member may for example include a surface area that rests on a corresponding surface area of the flange of the first body. Such a surface area has in some embodiments a size of about one square millimeter to about 10 square centimeters. In some embodiments, such a surface area is about 50 square millimeters to about 20 square centimeters in size. In some embodiments, such an area is about one square millimeter to about 50 square centimeters in size. In some embodiments, such a surface area of the flange-like disc-shaped holding member is in complete contact with the entire surface area of a portion of the flange of the first body.

In some embodiments of the connection system according to the second aspect, the first fluid-carrying body and the second fluid-carrying body are movably connected to each other. The first and the second fluid-carrying body may be pivotally connected to each other. For example, the first and the second fluid-carrying body may be connected to one another via one or more hinges.

In some embodiments of the connection system according to the second aspect, the flange-like disc-shaped holding member releasably rests on the flange of the first body. The flange-like disk-shaped holding member may be coupled to the flange of the first body. In some embodiments, the flange-like disc-shaped holding member is releasably coupled to the flange of the first body. In some embodiments, the flange-like disc-shaped holding member and the flange of the first body are movably coupled to one another.

The first side of the flange-like disk-shaped holding member defines a plane. If a membrane is present in the connection system, the plane defined by the first side of the holding member is typically parallel to a plane defined by the membrane.

In some embodiments of the connection system according to the first or the second aspect, the releasable connection member is screwable to the flange of the first body. In some embodiments, the releasable connection member defines a clamping device.

In some embodiments of the connection system according to the first or the second aspect, the disc-shaped holding member is connected to the connection member via a snap-in connection. To this end, the connection member typically includes a resilient member that interacts with the disk-shaped holding member. The connection member may also have a corresponding element which is elastic. In some embodiments, at least essentially the entire connection member is resilient.

In some embodiments of the connection system according to the first or the second aspect, the side of the disc-shaped holding member adapted for surface-to-surface contact with the flange of the first body, or the side resting on the flange of the first body, includes a peripheral guide edge. The guide edge is adapted for being in contact with the outer side of the flange. In some embodiments, the peripheral guide edge is adjacent to the peripheral outer edge of the disc-shaped holding member. In some embodiments, the peripheral guide edge adjoins the peripheral outer edge of the disc-shaped holding member.

In some embodiments, the side of the disk-shaped holding member that is adapted for surface-to-surface contact with the flange of the first body is adapted to contact the flange of the first body, or adapted for being in contact with the flange of the first body or to rest on the flange of the first body gene, includes a peripheral hook member. The peripheral hook member is adapted to at least partially envelop the outer side of the flange of the first body. In some embodiments, the peripheral hook member may be adjacent to the peripheral outer edge of the disk-shaped holding member. In some embodiments, the peripheral hook member adjoins the peripheral outer edge of the disc-shaped holding member. In some embodiments, the peripheral hook member may be arranged on the peripheral guide edge. In some embodiments, the peripheral hook member may be integrated into the peripheral guide edge. A respective hook member may essentially consist of a solid, non-pliable material, it may also entirely consist of a solid, non-pliable material.

In some embodiments, the side of the disk-shaped holding member, which is adapted for surface-to-surface contact with the flange of the first body or which is adapted to be in contact with or rest on the flange of the first body, includes two peripheral hook members. The two peripheral hook members are arranged at opposite ends of the disc-shaped holding member. The two peripheral hook members are both arranged on the side of the flange of the first body which is adapted for surface-to-surface contact with the flange of the first body, or on the side of the disc-shaped holding member which is resting on the flange of the first body. Both peripheral hook members may be adjacent to the peripheral outer edge of the disc-shaped holding member. Both peripheral hook members may adjoin the peripheral outer edge of the disc-shaped holding member.

In some embodiments, the connection member contains a clamping lever that is adapted to at least partially encircle the flange of the first body. The connection member may also essentially consist of a clamping lever which is adapted to at least partially grip around the flange of the first body. In some embodiments, a respective clamping lever defines the connection member. The connection member in one embodiment consists of such a clamping lever.

In some embodiments, the clamping lever may grip around the peripheral outer edge of the disc-shaped holding member. Typically, in such embodiments the clamping lever is connected to the holding member on the side of the disc-shaped holding member facing away from the flange. The clamping lever may then also be designed in such a way that it may in a movable way releasably grip around the peripheral outer edge of the disc-shaped holding member. In some embodiments, where the side of the disc-shaped holding member that is designed for surface-to-surface contact with the flange of the first body or the side of the disc-shaped holding member that rests on the flange of the first body has a peripheral guide edge, the peripheral guide edge may contain recesses into which the clamping lever can engage. In some embodiments, where the side of the disc-shaped holding member which is designed for surface-to-surface contact with the flange of the first body has a peripheral guide edge, the clamping lever may be designed to grip around the peripheral guide edge.

In some embodiments, the disc-shaped holding member includes two or more clamping levers adapted to at least partially grip around the flange of the first body. The clamping levers may be arranged axially offset from each other at positions on a peripheral edge of the disc-shaped holding member. Two clamping levers may for example be arranged at opposite ends of the disc-shaped holding member. The two or more clamping levers are adapted to at least partially grip around the flange of the first body. In some embodiments, the disc-shaped holding member at least essentially consists of two clamping levers. In some embodiments, the disc-shaped holding member includes three or more clamping levers.

In some embodiments, the connection member includes a clamping lever and a hook member. In some embodiments, the connection member includes a plurality of clamping levers and a plurality of hook elements.

In some embodiments of the connection system according to the first or the second aspect, the connection member is defined by a circumferential connection clamp, a tri-clamp connection, a locking ring and/or a substantially U-shaped clamp. A locking ring may include one or more undercut holding devices. Such an embodiment is for example depicted in FIG. 13.

In some embodiments, the connection member includes one or more clamping levers. Such a clamping lever is flexibly coupled to the disc-shaped holding member and at least partially grips around the flange of the first body. The connection member may also consist of one or more respective clamping levers. For example, a respective clamping lever may be movable around an axis that corresponds to the position at which the clamping lever is coupled to the disc-shaped holding member. The clamping lever may be connected to the disc-shaped holding member.

In some embodiments, the connection member includes an arm that is movably coupled to the disk-shaped holding member. The connection member may also consist of a movable arm coupled to the disc-shaped holding member. The arm at least partially grips around the outer side of the flange of the first body and the peripheral outer edge of the disc-shaped holding member. The arm may for instance be attached to the peripheral outer edge of the disc-shaped holding member. To lock the arm in place, there may for example be provided, on the peripheral outer edge of the disc-shaped holding member, a form-locking receiving or supporting element such as a joint or a riveted or frame-shaped holder, into which the arm is releasably inserted. In some embodiments, the connection member includes a plurality of movable arms coupled to the disc-shaped holding member. For example, there may be two or three movable arms provided, which are coupled to the disc-shaped holding member.

In some embodiments, the connection member includes a first thread and the disk-shaped holding member includes a second thread. The first and the second thread fit into each other and are screwed together. The first and the second thread may be a female and a male thread. For example, the connection member and the disc-shaped holding member may be connected in the form of a Luer-Lock.

In some embodiments, the connection member has a circumferential wall which encompasses the peripheral outer edge of the disc-shaped holding member. The circumferential wall includes a pair of axially opposed openings and the peripheral outer edge of the disc-shaped holding member includes a pair of axially opposed protrusions. The pair of axially opposed protrusions is retained in the pair of axially opposing openings in the form of a bayonet lock.

In some embodiments, the connection member includes a clamp consisting of at least two movable elements, which grip around the peripheral outer edge of the disc-shaped holding member and around the flange of the first body. Such a clamp may consist of two hinged elements, which can be hinged open and which may for example be connected via a hinge. Such a clamp may be constructed according to a known mechanism known as BioClamp®, ReadyClamp®, Tri-clamp or Tri-clover.

The connection member may be defined by a circumferential connecting clip, by a tri-clamp clamping connection, by a locking ring and/or by a substantially U-shaped clamp.

In some embodiments, the connection member is movable, e.g. rotatably or retractably slidably (in or out) connected to the first and/or the second body. The first and/or the second body may for instance include a rail or a bar and the connection member may contain a pin. The first and/or the second body may also contain a pin and the connection member may include a rail or a bar. The bar or the rail may be dimensioned and arranged in such a way that it allows guiding and securing the pin.

In some embodiments of the connection system according to the first or the second aspect, the connection member is defined by a substantially U-shaped clamp having an upper and a lower element. In these embodiments, the disc-shaped holding member is arranged between the upper and the lower element of the substantially U-shaped clamp. The substantially U-shaped clamp may include a pair of legs arranged parallel to the plane of the flange. In some embodiments, the substantially U-shaped clamp may be defined by an upper pair of legs, a lower pair of legs, and a sidewall. The side wall may connect one upper and one lower leg, respectively.

In some embodiments of the connection system according to the first or the second aspect, the connection member is defined by a combination of at least one fixed hook element and at least one clamping lever, by a combination of at least one fixed hook element and at least one snap connection, by a combination of two or more clamping levers and/or a combination of a substantially U-shaped clamp and at least one fixed hook element.

In some embodiments of the connection system according to the first or the second aspect, the connection member includes an essentially U-shaped clamp and the second side of the disk-shaped holding member includes a guide edge. The guide edge is adapted to contact the outer side of the flange of the first body.

In some embodiments of the connection system according to the first or the second aspect, the connection member includes an essentially U-shaped clamp with an upper pair of legs, a lower pair of legs and a side wall connecting each upper and each lower leg. In some embodiments, the connection member essentially consists of an essentially U-shaped clamp having an upper pair of legs, a lower pair of legs, and a side wall connecting each upper and each lower leg. The side wall includes an opening on the side of each leg. The disc-shaped holding member includes a pair of legs, which are arranged parallel to the plane of the flange of the first body. The holding member is arranged between the upper and lower members of the substantially U-shaped clamp. This allows the legs to hold and guide the connection member.

The pair of upper legs of the essentially U-shaped clamp of such a connection member is located on the side facing the second body, relative to the disk-shaped holding member. The pair of lower legs is arranged on the side facing the first body. The pair of upper legs includes in some embodiments a bar that is adapted to allow guiding and securing a pin that is mounted on the second body. In some embodiments, the pair of lower legs includes a bar that is adapted to allow guiding and securing a pin that is mounted on the first body.

In some embodiments, the pair of upper legs is at least essentially parallel to the plane of the flange of the first body. In some embodiments, the pair of lower legs is arranged at least essentially parallel to the plane of the flange of the second body. The pair of upper and/or lower legs typically defines a plane that is essentially parallel to the plane of the flange of the first body. In some embodiments, the pair of upper and/or the pair of lower legs is a pair of essentially symmetrical legs.

The disk-shaped holding member may also include a pair of legs. The pair of legs of the disc-shaped holding member may also be arranged at least essentially parallel to the plane of the flange of the first body. Such a pair of legs of the disk-shaped holding member may define a plane that is arranged essentially parallel to the plane of the flange of the first body. The pair of legs of the disk-shaped holding member typically points away in a parallel manner from a peripheral edge of the holding member. The pair of legs of the disc-shaped holding member may be fitted between the upper and the lower element of an essentially U-shaped clamp of the connection member in such a way that it allows them to hold and guide the clip. The pair of legs of the disc-shaped holding member may be fitted between a pair of upper legs and a pair of lower legs of an essentially U-shaped clamp of the connection member. In some embodiments, the pair of legs of the disc-shaped holding member is a pair of two legs that are essentially symmetrical to each other.

In some embodiments, the end of at least one of the legs of the disc-shaped holding member is shaped as a hook. The outer side of a U-shaped clamp of a connection member may in such an embodiment include a recess or an opening adapted to receive the hook.

Mounting a connection system for releasably force-fittingly coupling a first body to a fluid carrying system as disclosed herein involves contacting the first end of the first body with the second end of the second body. Such assembling also includes arranging the releasable connection member in such a way that the releasable connection member at least partially grips around the flange of the first body and the peripheral outer edge of the disk-shaped holding member (as a separate component) or the flange-like disk-shaped holding member, defining the second end of the second body. Mounting may also include bringing the releasable connection member, being in a position in which it at least partially grips around the flange of the first body and the peripheral outer edge of the disk-shaped holding member or the flange-like disc-shaped holding member, into a position where the first body is force-fittingly fixed to the second body.

According to a third aspect, there is provided a method of releasably force-fittingly coupling a first body to a fluid-carrying system via a fluid-tight membrane. The first body includes a first end with a flange. To the fluid-carrying system, an interior space of a second body is coupled. The second body includes a second end with a circumferential wall and an interior. The second end also contains an opening of the interior space, for example a central opening. A peripheral portion of the circumferential wall that is circumferential around the opening of the interior space defines a membrane contact portion. The circumferential wall is circumferential around the opening of the interior space. The circumferential portion that defines the membrane contact portion is generally in a plane that is defined by the opening of the interior space. Typically, the circumferential portion, which defines the membrane contact portion, points in the same direction as the opening of the interior space. The membrane contact portion is in contact with the membrane. In typical embodiments of the method according to the third aspect, the membrane contact portion is connected to the membrane.

The second end of the second body is furthermore in contact with a disc-shaped holding member. In typical embodiments, the second end of the second body is connected to this disk-shaped holding member. The disc-shaped holding member includes a passage, a first side, a second side and a peripheral outer edge. The first side of the holding member is in contact with the second end of the second body. Furthermore, the first side and/or the passage of the holding member is/are coupled to the membrane. In typical embodiments, the first side and/or the passage of the holding member is/are connected to the membrane. The second side of the holding member is designed for surface-to-surface contact with the flange of the first body.

The method according to the third aspect involves bringing into contact the disk-shaped holding member that is positioned at the second end of the second body, and the first end of the first body. The disc-shaped holding member and the first end of the first body are aligned in such a way that the second side of the disc-shaped holding member rests on the flange of the first body. Subsequently, a releasable connection member is arranged in such a way that it at least partially grips around the flange of the first body and the peripheral outer edge of the disc-shaped holding member. Thereby the disc-shaped holding member is force-fittingly fixed to the first body in a reversible manner by means of the connection member.

In some embodiments of the method according to the third aspect, the disc-shaped holding member and the first end of the first body are first arranged in such a way that the second side of the disc-shaped holding member rests on the flange of the first body. Subsequently, the releasable connection member is brought into a position in which it is in a plane with the flange of the first body and the peripheral outer edge of the disc-shaped holding member. From this position, the releasable connection member can, within in the same plane, be brought into a position in which it can at least partially grip around the flange of the first body and the peripheral outer edge of the disc-shaped holding member. In this position, the first body and the disc-shaped holding member, and thereby the first body, and the second body are in releasable contact with each other. Thereafter, the releasable connection member is brought into the position in which it at least partially grips around the flange of the first body and the peripheral outer edge of the disc-shaped holding member. As a result, the disc-shaped holding member is reversibly force-fittingly fixed to the first body by means of the connection member.

The interior space of the second body includes a wall. This wall is generally the circumferential wall of the second end of the second body. In some embodiments of the method according to the third aspect, the membrane is substantially more flexible than this wall of the interior space of the second body.

According to a fourth aspect, there is provided a method releasably force-fittingly coupling the interior space of a first fluid-carrying body to the interior space of a second fluid-carrying body. The first fluid-carrying body includes a first end with a flange. Furthermore, in the first end of the first fluid-carrying body there is arranged an outlet of the interior space of the first body. The second fluid-carrying body includes a second end. This second end defines a flange-like disk-shaped holding member. The flange-like, disk-shaped holding member includes a peripheral outer edge and a central opening. This central opening is an opening of the interior space of the second fluid-carrying body. The holding member furthermore includes one or more arms. The connection system also includes a connection member that is designed to at least partially grip around the peripheral outer edge of the flange-like disk-shaped holding member and the flange of the first body. In this way, the holding member is force-fittingly fixable to the first body by means of the releasable connection member. In the method according to the fourth aspect, the flange-like, disc-shaped holding member is connectably coupled to the flange of the first body in such a way, that the holding member rests on the flange of the first body. Subsequently, the connecting member is placed on the flange-like disc-shaped holding member and the flange of the first body, in such a way, that the connection member at least partially grips around the peripheral outer edge of the flange-like disc-shaped holding member and the flange of the first body. As a result, the flange-like, disk-shaped holding member is reversibly force-fittingly fixed to the first body by means of the connection member.

In typical embodiments of the method according to the fourth aspect, the connection member includes an essentially U-shaped clamp with two legs. The essentially U-shaped clamp includes one or more recesses into which the arm or the arms of the holding member are insertable.

In some embodiments, the method according to the fourth aspect includes providing the first fluid carrying body and the second fluid carrying body.

In some embodiments, the method according to the fourth aspect is a method for sterile or aseptic coupling the interior space of a first fluid carrying body to the interior space of a second fluid carrying body.

A connection system for releasably force-fittingly coupling the interior space of a first fluid-conducting body to the interior space of a second fluid-carrying body as disclosed herein may also be in a state in which the holding member has not yet been force-fittingly fixed to the first body by means of the releasable connection member. In this state, the arm of the holding member is for example not inserted into a recess of an essentially U-shaped clamp of the connection member. Mounting this connection system generally involves bringing the first end of the first body, which includes a flange, into contact with the second end of the second body, which defines a flange-like disc-shaped holding member. Mounting also includes arranging the releasable connection member in such a way that the releasable connection member at least partially grips around the flange of the first body and the peripheral outer edge of the holding member. As an example, the arm of the holding member is inserted into the recess of an essentially U-shaped clamp of the connection member. Mounting may also involve bringing the releasable connection member, being in a position where it at least partially grips around the flange of the first body and the peripheral outer edge of the holding member, into a position where the first body is force-fittingly fixed to the second body. For example, the arm of the holding member may be locked in place in the recess of the clamp.

The foregoing summary is not limiting and further features and advantages of the device disclosed herein will be apparent from the following detailed description, the drawings and the claims.

BRIEF DESCRIPTION OF THE DRAWINGS

FIG. 1A shows the connection system as a cross-section, while FIG. 1B shows the connection system in plan view. The connection system includes a membrane (1) and a second body (3) with an interior space. It is connected to a first body (5) that includes a flange (25). The second body (3), which is coupled to a fluid carrying system, includes a second end with an interior space (23) and a circumferential wall (22). An outlet (43) is covered by the membrane (1). The circumferential wall (22) includes a membrane contact portion (9) circumferential around the outlet (43) and connected to the membrane (1). The second end of the second body (3) defines a flange-like, disc-shaped holding member (2) with a peripheral outer edge (24). A releasable connection member (4) circumferentially grips around the peripheral outer edge (24) of the holding member (2) and the flange (25) of the first body (5). As can be taken from FIG. 1B, the connection member (4) does not entirely grip around the holding member (2) and the flange (25) of the first body (5) over their complete circumference, but only by a portion that defines about half of the entire circumference. The dimensions of the individual components and features are not true to scale, but are adapted for the sake of clarity.

FIG. 2 depicts a further connection system according to an embodiment disclosed herein. It contains a first body (5) with a flange (25). The connection system includes a second body (3) in the form of a housing. An end of the second body (3) having an interior space (23) includes a circumferential wall (22) with a circumferential bead (62) and a recess (28) as a retrace. The circumferential bead (62) circumferentially surrounds an outlet (43) and includes a circumferential membrane contact portion (9). The outlet (43) of the second body (3) is covered by the membrane (1). Between the first (5) and the second body (3) there are arranged a membrane (1) and a disc-shaped holding member (2) with a circumferential wall (26). The wall (26) of the disc-shaped holding member (2) is in contact with the recess (28) of the second body (3). A connection member (4) grips around a peripheral outer wall (24) of the holding member (2) and the flange (25) of the first body (5). The dimensions of the individual components and features have been adapted for the cross-sectional view for illustration purposes.

FIG. 3 depicts an embodiment of the connection system where the first body (5) is a measuring element and the second body (3) is a measuring chamber. A cylindrical end of the second body (3) with a cylinder interior (23) includes a circumferential wall (22) with a circumferential bead (62). The circumferential bead (62) contains a circumferential membrane contact portion (9). On a first side of the disc-shaped holding member (2) facing the second body (3), there is a wall (26) which contacts a portion (28) of the circumferential wall (22) that faces away from the cylinder interior (23). Furthermore, this portion (28), which can also be taken to define a recess (28) as a retrace, includes a groove (32). A bead (41) of the wall (26) of the wall (26) of the disc-shaped holding member (2) is located in the groove (32). A guide edge (8) is provided on the peripheral outer wall (24) of the disc-shaped holding member (2), which contacts the flange (25) from the outside. The connection member (4) grips around the guide edge (8).

FIG. 10A depicts a section of a connection system, in which an embodiment of the connection member (4) that is similar to the embodiment shown in FIG. 8, together with an embodiment of the disc-shaped holding member (2) as shown in FIG. 9, is arranged between the first body (5) and the second body (3). The connection member (4), and thereby the entire connecting system, is in a closed state in which the arms (10) with hooks (27) of the disc-shaped holding member (2) protrude as far as possible from the recesses of the connection member (4). As a result, the connection member (4) grips around the flange of the first body (5) covered by the connection member (4). The insertion element (37) of the disc-shaped holding member (2) is locked in place in a recess of the connection member (4).

FIG. 4. The second body (3) has two annular collars (51). The connection system is in closed position.

FIG. 11A depicts a further embodiment of the connection system, in which a first body (5), a fluid-tight membrane (1), a disk-shaped holding member (2) and a releasable connection member (4) are included. The connection member (4) is designed as a U-shaped clamp and is in a closed position, in which the U-shaped clamp is in contact (cf. FIG. 10) with a peripheral portion of the disc-shaped holding member (shown in white). The connection system is connected to a first body (5) that includes a flange (25). The second body (3) has an interior space (23) which ends in an opening (43). The opening (43) is framed by a peripheral wall (22) that includes a circumferential bead (62) adjacent to the opening (43). The circumferential bead (62) includes a circumferential membrane contact portion (9) on which the membrane (1) rests. Furthermore, the circumferential wall (22) has a groove (32). A bead (41) of a wall (26) of the disc-shaped holding member is arranged in the groove (32). The circumferential wall (22) further includes a projecting wall portion (20) with a guide bar (18). The guide bar (18) is in contact with a bar (19) of the connection member (4). The peripheral outer wall (24) of the disc-shaped holding member is seated in a guide edge (8) pointing in the direction of the first body (5), which is in contact with the flange (25) from the outside. The connection member (4) grips around the guide edge (8) and the flange (25). The dimensions of the interior of the fluid-carrying system within the second body (3) are not true to scale, but have been adapted for the sake of clarity. The proportions of the dimensions of the surrounding wall (22), the membrane (1), the flange (25), the connection member (4) and the holding member are essentially depicted true to scale and have only been reduced for the reproduction as a figure.

FIG. 11B depicts the embodiment shown in FIG. 11A from above. Here, too, the connection member (4) is in a closed position, in which the U-shaped clamp thereof is in contact with a circumferential portion of the disk-shaped holding member (2) (cf. FIG. 10). The illustrated ratios essentially correspond to the original of the embodiment shown, the size has been reduced only for the reproduction as a figure. As can be seen from the figure, the arms (10) of the disc-shaped holding member (2) extend through the recesses of the connection member (4), which includes the handle element (12). A bail (47) of the holding member (2) can be seen in plan view, in which it partially covers the connection member (4).

FIG. 11C depicts the embodiment shown in FIG. 11A and FIG. 11B from a lateral perspective, namely along an axis of the second body (3). The connecting element (4) in an embodiment as a U-shaped clamp is again in a closed position, in which it in contact with a peripheral portion of the disc-shaped holding member (2). It should be noted that in this perspective, the connection member (4) does not grip around the flange (25), since this grip is present only on the side facing the viewer and facing away from the viewer. Instead, there are recognizable hook elements (7) of the disk-shaped holding member (2). A bail (47) of the disc-shaped holding member (2) locks in place a mount (45) of the connection member (4). The depicted ratios essentially correspond to the original of the embodiment shown, the size has been reduced only for reproduction as a figure.

FIG. 10). The portion of the connection member (4) which includes a bar (19) is shifted relative to the second body (3), and especially relative to the wall portion (20), in such a way that it is not visible in the cross-section shown (cf. e.g. FIG. 10B). In this position, the connection member (4) does not grip around the peripheral outer edge (24) of the holding member, and in the region of the depicted cross section the guide edge (8) of the holding member is in contact with the surroundings, but not with the connection member (4).

FIG. 11B. Of the arms (10) of the disk-shaped holding member (2), only the end with the hook (27) extends through the recesses of the connection member (4).

FIG. 13C shows a cross section of the connection system in locked form, while in FIG. 13A the cross section of the connection member (4) is laterally skewed in accordance with the locking mechanism. FIGS. 13B and 13D accordingly depict a first unlocked position and a second locked position of the locking ring. FIG. 13E depicts the second body (3) with the connection member (4) slanted from above, that is from the perspective of the first body (5) diagonally opposite. FIG. 13F depicts the first body (5) slanted from above, that is, from a perspective diagonally sideways through the second body (3). The flange (25) of the first body (5) includes protrusions (40) for locking the locking ring in place.

FIGS. 14A-14F depict an embodiment of the connection system, in which the connection member (4) is defined by two opposing clamping levers. In this embodiment, the clamping levers are rotatably coupled to the peripheral outer edge (24) of the holding member (2). FIG. 14A and FIG. 14C depict the connection system with released clamping levers, while FIG. 14B and FIG. 14D depict the connection system with locked clamping levers. FIG. 14F and FIG. 14E each depict an enlarged section in cross-sectional view of the positions shown in FIG. 14A and FIG. 14C, and in FIG. 14B and FIG. 14D, respectively. The clamping levers (4) grip around the peripheral outer edge (24) of the holding member (2) and, in the locked state, grip around the flange (25) of the first body (5).

FIGS. 16A-16I depict an embodiment of the connection system in which the connection member (4) is defined by a pivotable arm (30) with a tongue (49), which can latch into a rivet-shaped protrusion (42) that is arranged at the peripheral outer edge of the disc-shaped holding member (2). FIG. 16A depicts the connection member (4) in a released state, while in FIG. 16B the tongue (49) of the connection member (4) is fixed in the protrusion (42). In FIG. 16A it can be seen that the holding member rests on the flange (25) of the first body (5). FIG. 16C is a perspective view of the connection member (4) arranged between the second body (3) and the first body (5), defined by a pivotable arm (30) having a tongue (49). In this state, the arm is not latched in the rivet-shaped protrusion (42). The view is slanted from above, i.e. from the direction of the second body (3). The proportions of the dimensions of the arm (22), the first body (5), the second body (5), the tongue (49), the rivet-shaped protrusion (42) and the holding member (2) are essentially represented true to scale and reduced only for reproduction as a figure. FIG. 16D depicts the disc-shaped holding member (2) with the arm (30) located thereon and the rivet-shaped protrusion (42) from below, i.e. from the direction of the first body (5). The rivet-shaped protrusion (42) marked by a circle is shown in FIG. 16E in approximately fivefold magnification. A handle element (54) is coupled to a toothed rack (53) via a pin (56). FIG. 16F depicts the disc-shaped holding member (2) with the arm (30) located thereon and the rivet-shaped protrusion (42) slanted from above, i.e. from the direction of the second body (3). Again, a state is shown in which the arm (30) is not latched into the rivet-shaped protrusion (42). FIG. 16G depicts, from the same perspective as FIG. 16F, the disc-shaped holding member (2) with the arm (30) located thereon, which, however, is latched into the protrusion (42) in the rivet-shaped protrusion. FIG. 16H depicts the disk-shaped holding member (2) with the arm (30) and the rivet-shaped protrusion (42) in the same latched state slanted from below, i.e. from the direction of the first body (5). The rivet-shaped protrusion (42) of FIG. 16H marked by a circle is shown in FIG. 16I in approximately fivefold magnification. The handle member (54) is coupled to the toothed rack (53) via a pin (56).

FIGS. 18A-18H depict elements of a connection system. FIG. 18A depicts the connection system shown in FIG. 17 in a lockable open state, in which the flange-like disk-shaped holding member (2) of the second body (3) rests on the flange (25) of the first body (5). A hook (39) fixes the first and the second body relative to one another. Releasable protective films (48) block the respective interior space of the first (5) and the second (3) body. FIG. 18B depicts an unfolded state in which the first body (5) and the second body (3) are pivotally coupled to each other only by the hinge. The hook (39) does not fix the first and the second body together. FIG. 18C depicts schematically from above an arrangement essentially corresponding to the one of FIG. 18A, that is from the direction of the second body (3). The state of the connection system differs from the state shown in FIG. 18A in that the protective films (48) are removed. Legs (10) of the flange-like disc-shaped holding member (2) and arms (31) of the connection member (4) can be seen. FIG. 18E and FIG. 18F show the state depicted in FIG. 18C from two different lateral perspectives. FIG. 18D depicts the arrangement of FIG. 18C in a closed and locked state, in which the connection member (4) fixes the first and the second body by gripping around the flange (25) and the peripheral outer edge of the holding member by about half, or a few degrees more than half of the respective circumference (see below). FIG. 18G and FIG. 18H depicts the state shown in FIG. 18D from two different lateral perspectives.

DETAILED DESCRIPTION

Figure 1A:
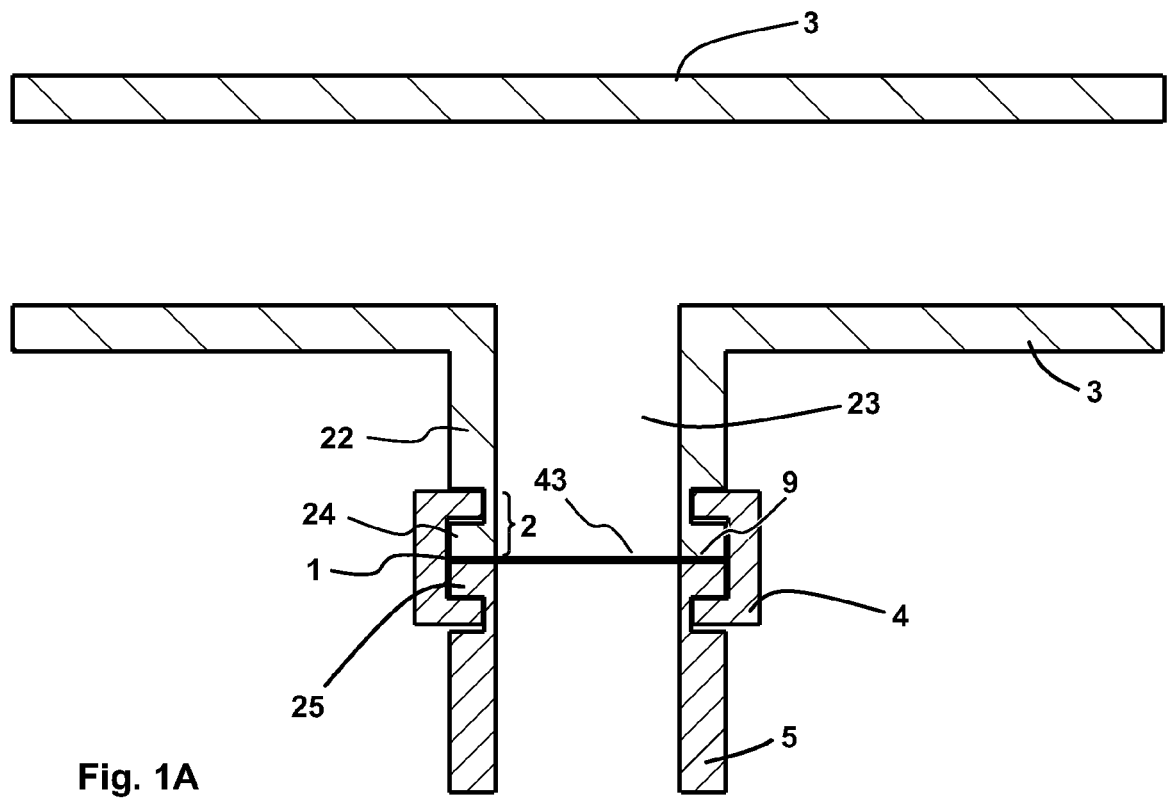
FIGS. 1A-1B depict a connection system as disclosed herein in a general schematic representation.
Figure 1B:
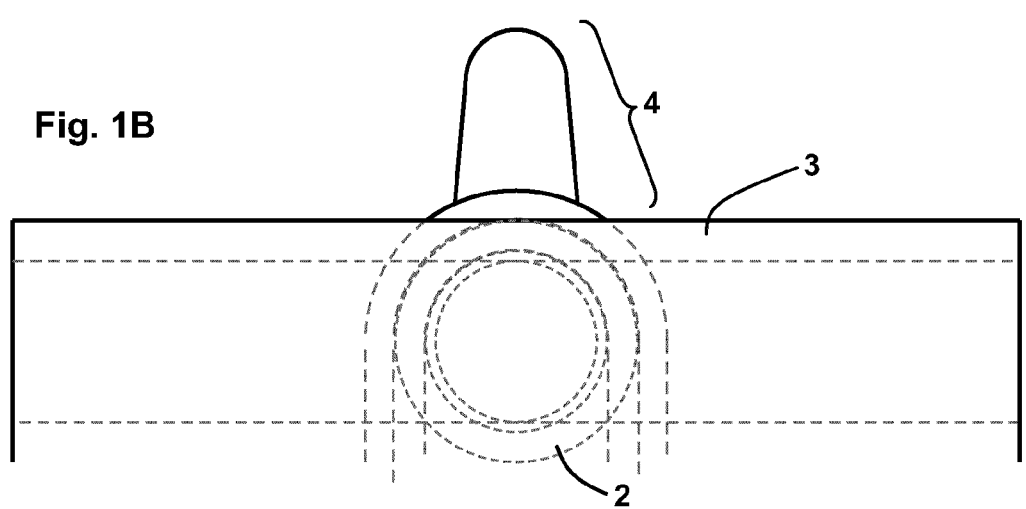

A connection system disclosed herein generally allows a robust and defined mechanical coupling of a first body to a fluid-carrying second body, such as e.g. a measuring element to a single use component. The connection can typically be achieved by a simple mounting. In some embodiments, this mounting can even be performed safely and reliably with just one hand. In particular, a connection member, located on a holding member located on the second body and fixable to the first body, contributes to the connection. In some embodiments the fluid is a liquid such as an aqueous medium.

This can be achieved, on the one hand, by the fact that the coupling of the first and the second body is typically carried out in a very confined space by directly pressing the disc-shaped holding member against the flange of the first body, e.g. the measuring element by means of the connection member (4). The disk-shaped holding member on the other hand connects the membrane directly to the second body, e.g. the measuring chamber, in a confined space. In embodiments where a measuring element and a measuring chamber are coupled, this thereby ensures reliable force closure and thus reliable force measurement of the compressive force acting on the membrane surface.

In addition, the configuration of the connection member of a connection system disclosed herein offers the possibility of a simple and safe mounting. With the connection system disclosed herein, a safe disassembly and reassembly can also be ensured.

The membrane is dimensioned to close the interior space of the second body from the ambience by covering the opening of the second end of the second body. In some embodiments, the membrane can be positioned in an accurately fitting manner in the passage of the holding member and thereby close the same. In some embodiments, the membrane may be sized to overlap with a circumferential membrane contact portion of the second end of the second body. In a plane of the opening of the second end of the second body the membrane may have a width that is greater than this opening of the second end of the second body.

In some embodiments, the second end of the second body may include an element that extends at least partially into the passage of the holding member, for example in the form of a circumferential bead of the circumferential wall of the second end of the second body. In some embodiments, such an element, such as a bead or a bar, may be in contact with a surface area of the disk-shaped holding member facing the interior space of the second end of the second body, for example butting against the same in an accurately fitting manner. Such an element may in some embodiments be in contact with the membrane. As an example, in some embodiments, a bead may define a membrane contact portion circumferential around the opening of the second end of the second body which in the mounted state faces the first body. This membrane contact portion may be in contact with the membrane. This membrane contact portion may be fixedly connected to the membrane, for example by welding, gluing or sealing. In some embodiments, a bead may include a surface area facing away from the interior space of the second end of the second body, for example a circumferential surface area. Such a surface area facing away from the interior of the second end of the second body may, in some embodiments, be in contact with the membrane. This surface area may be firmly connected to the membrane, for example by welding, gluing or sealing. In some embodiments, the membrane may be arranged between such a surface area facing away from the interior space of the second end of the second body and the disk-shaped holding member, for example in a sandwich arrangement. The membrane may be positioned in an accurately fitting manner between the respective surface area, e.g. a bead or a bar, and the disc-shaped holding member.

As explained in the foregoing, in some embodiments in which the disc-shaped holding member defines a terminal design component of the second end of the second body, the connection system does not include a membrane. In such embodiments, the connection system serves in releasably force-fittingly coupling an interior space of the first fluid-carrying body to an interior space of the second fluid-carrying body.

Unless otherwise stated or the context clearly indicates another meaning, the following terms and expressions, when used in this document including the description and claims, have the definitions given below.

The term "consisting of" as used in this document means inclusive and limited to what follows the term "consisting of". The term "consisting of" thus indicates that elements listed are required or necessary and that no further elements may be present. The term "essentially consisting of" is understood to mean that any elements defined according to the term are included and that other elements, for example in a sample or a composition, may be present which do not modify the activity or effect indicated for the elements specified in this document, that is they do not adversely affect it and do not contribute to the same. In other words, the term "essentially consisting of" indicates that the defined elements are required or necessary, but that other elements are optional and may or may not be present, depending on whether they are relevant to the effect or effectiveness of the defined elements are or not.

The word "about" as used herein refers to a value being within an acceptable error range for the particular value as determined by one of ordinary skill in the art. This will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects as disclosed in this document. In this context "about" may refer to a range of up to 10% above and/or below a certain value. In some embodiments, "about" refers to a range above and/or below a certain value that is up to 5%, such as up to up to 2%, above and below a given value. In some embodiments, "about" refers to a range above and/or below a certain value that is up to 1% above and below a given value. In some embodiments, "about" refers to a range above and/or below a certain value that is up to 0.5% above or below that value. In one embodiment "about" refers to a range up to 0.1% above and below a given value.

The conjunctive expression "and/or" between multiple elements, as used herein, is understood to encompass both individual and combined options. For example, if two elements are linked by "and/or", a first option concerns the use of the first element without the second one. A second option concerns the use of the second element without the first one. A third option involves the use of the first and second elements together. It is understood that any one of these options falls within the meaning of the term and thus meets the conditions of the term "and/or" as used in this document.

Singular forms such as "a", "an" or "the" include plural references when used in this document. Thus, for example, reference to "a cell" refers to both an individual cell as well as a plurality of cells. In some cases, the term "one or more" is used explicitly to indicate in each case that the singular form includes the plural form. Such explicit indications do not limit the general meaning of the singular form. Unless otherwise indicated, the term "at least" preceding a series of elements is to be understood to refer to every element in the series. The terms "at least one" and "at least one of" include for example, one, two, three, four, or five or more elements.

Figure 15:
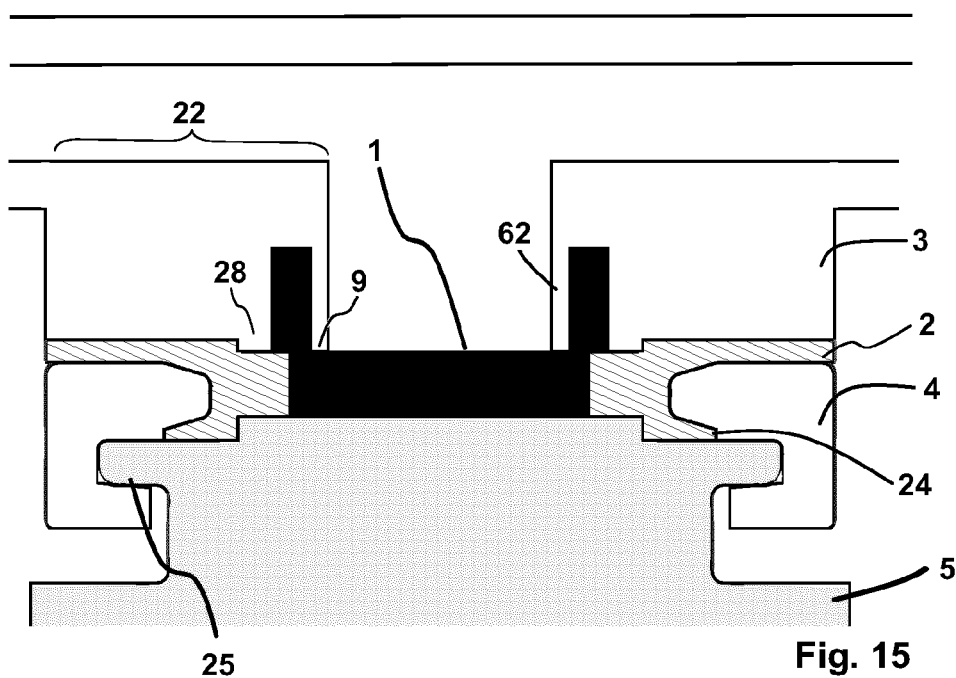
FIG. 15 depicts an embodiment of the connection system, in which the connection member (4) has a slightly angled surface adjacent to the flange (25). The flange (25) includes a surface adjacent to the connection member (4) that conically tapers. When the connection member (4) is slid onto the flange (25), this results in a tension which contributes to establishing a firm connection.
Figure 16A:
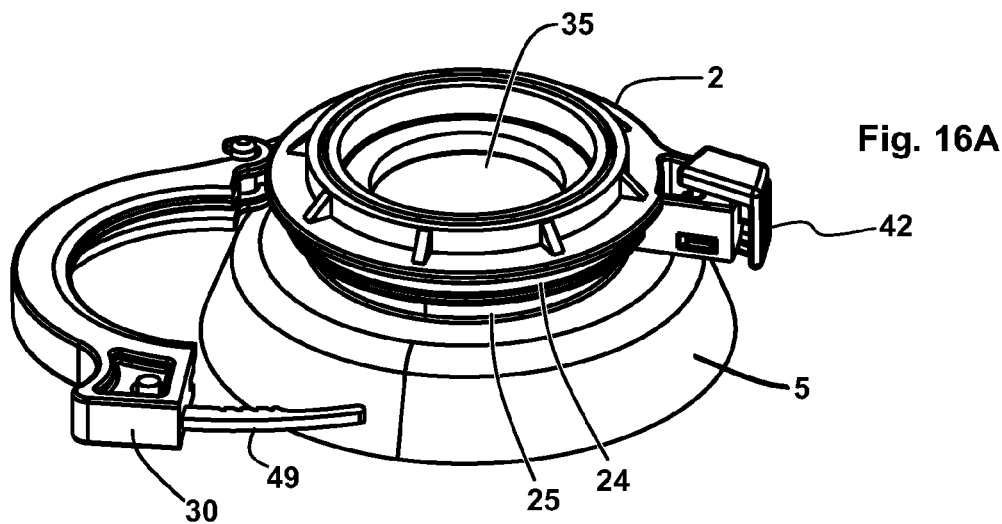
Figure 16B:
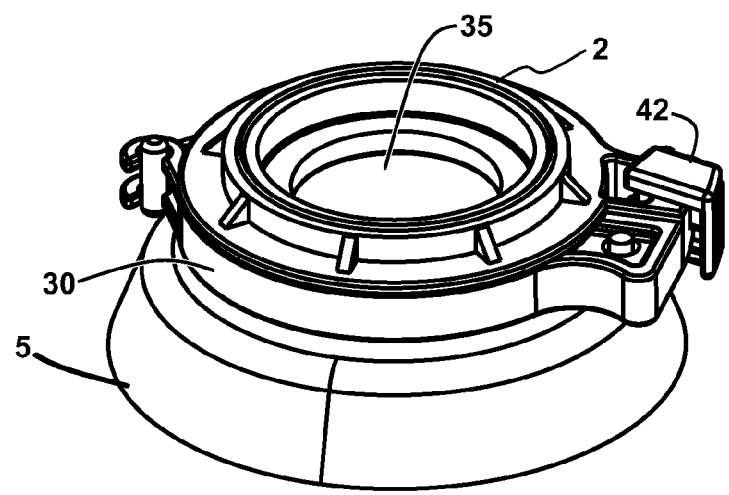

In all embodiments disclosed herein, the disk-shaped holding member includes a peripheral outer edge, which a releasable connection member may at least partially grip around. The disc-shaped holding member may include a plurality of peripheral outer edges. One or more of such peripheral outer edges may extend axially outward further than other peripheral outer edges. In such embodiments, a grip at least partially around any peripheral outer edge of a releasable connection member may occur to establish a connection. In some embodiments, where there is more than one peripheral outer edge, a releasable connection member may at least partially grip around more than one outer peripheral edge. In some embodiments, a respective peripheral outer edge gripped around is the outermost peripheral outer edge included in the releasable connection member. In some embodiments, a respective peripheral outer edge gripped around is not the outermost peripheral outer edge included in the releasable connection member, cf. e.g. FIG. 15 or FIG. 16. In some embodiments, e.g. the one shown in FIG. 16, in the mounted state the peripheral outer edge of the disc-shaped holding member, that the releasable connection member at least partially grips around, directly abuts the flange of the first body. For example, FIG. 16A shows a connection member defined by a movable arm (30) having a tongue (49) and a rivet-shaped protrusion (42). Above the flange (25) of the first body (5) a wall is just recognizable, which defines a peripheral outer edge (24). As shown in FIG. 16B, this peripheral outer edge (24) is the peripheral outer edge, that the connection member partially grips around.

Provided by this disclosure is a connection system for releasably force-fittingly coupling a first body (e.g., a first body (5)) to a second fluid carrying body (e.g., a second body (3)). The first body includes a first end with a flange (25), for example with an annular flange.

Force-fittingly coupling, as used herein, means coupling a first to a second body in which a state is generated in which the first body and second body are prevented from moving against each other. As an example, it prevents the first and the second body rom shifting or twisting against each other. Typically, the state of force-fittingly, i.e. nonpositively coupling in a system disclosed herein is achieved by locking the same in place. For example, a sliding or rotary movement of a connection member may be possible up to a pre-selected end position, in which a locking mechanism is triggered. For example, a locking element may latch and thereby prevent a further or backward sliding or rotating movement. It should thus be apparent that force-fittingly coupling may, for example, involve a form fit at one or more elements of the connection system.

In typical embodiments, a connection system disclosed herein achieves a force-fitting connection of the respective first and the second body. In some embodiments, the flange of the first body includes a contact surface facing the second body. The disc-shaped holding member may in such embodiments include a first side facing the second body. The disc-shaped holding member may include a second side, which faces the second body. This second side may include a contact surface which is designed for surface-to-surface contact with the flange of the first body, or which is designed to rest on the flange of the first body. A connection system disclosed herein is designed to prevent movement of a respective contact surface of the disc-shaped holding member relative to the contact surface of the flange of the first body, including movement along the contact surface. In order to overcome the force-fitting connection, a force is generally required that is sufficient to cause mechanical damage to one or more components of the connection system, typically to one or more components of the releasable connection member.

The connection system described herein includes the second body and a releasable connection member (e.g., a connection member (4)). In this case, the second body may either (a) include a second end with an interior space (e.g. an interior space (23)) and a peripheral wall (e.g. a wall (22)) or (b) include a second end, which opens into a flange-like, disk-shaped holding member (e.g, a holding member (2)) with a peripheral outer edge (e.g., an outer edge (24)). In the second case, the disc-shaped holding member thus defines an end of the second body, while in the first case it defines a distinct component.

When the second body includes a second end with an interior space and a circumferential wall, the connection system furthermore includes a disk-shaped holding member (e.g., a holding member (2)). The disc-shaped holding member includes a passage (e.g., a passage (35)), a first side, a second side, and a peripheral outer edge (e.g., an outer edge (24)). The first side and/or the passage of the holding member is/are coupled to the membrane. On the first side of the holding member there is arranged a circumferential wall (e.g., a wall (26)) adapted to be connected to the circumferential wall of the second body. The second side of the holding member may for example be adapted for a surface-to-surface contact with the flange of the first body, or for resting on the flange of the first body.

In embodiments where the second body includes a second end with an interior space and a peripheral wall, the second body typically includes a port, such as an outlet (e.g., an opening (43)). In some such embodiments, the circumferential wall includes a membrane contact portion (e.g., a membrane contact portion (9)) circumferential around the port, which may be connected to the membrane or which is connected to the membrane.

When the second body includes a second end, ending in a flange-like disc-shaped holding member, this holding member includes a central port such as an outlet (e.g., an opening (43)) of the interior space of the second fluid-carrying body.

The connection member is designed to at least partially grip around the peripheral outer edge of the holding member and the flange of the first body, such that the holding member is force-fittingly fixed to the first body by means of the connection member.

In some embodiments, the first body is not fluid carrying. In some embodiments, the first body does not include an interior space. In some embodiments, the first body includes an interior space, however, it is not fluid-carrying. By way of an example, in embodiments in which the connection system includes a disk-shaped holding member as a distinct component, the first body may not include an interior space. Also, in embodiments in which the connection system includes a disc-shaped holding member, the first body may be a non-fluid-carrying body.

In some embodiments, both the first and second body are fluid-carrying. For example, in embodiments in which the second body includes a second end which ends in a flange-like, disk-shaped holding member, both the first and the second body may be fluid-carrying. In some embodiments, the first body is coupled to the second fluid carrying body is via a fluid tight membrane. In such embodiments, the connection system includes the membrane and the second body with an interior space. In some embodiments, there is arranged a circumferential bar or a circumferential bead (e.g., a bar or bead (62)) on the first side of the holding member or on the flange-like disc-shaped holding member.

In some embodiments, the second end of the second body includes a membrane contact portion. In some embodiments this membrane contact portion faces the first body. As already indicated above, a circumferential wall of the second body, for example an annular peripheral wall, may for example contain such a membrane contact portion. In some embodiments, the second end of the second body, independently of the membrane contact portion, includes a portion that faces the first body and that is different from the membrane contact portion. Such a portion, which faces the first body, may for example adjoin the membrane contact portion. As an illustrative example, in an embodiment in which the second body includes a second end, which opens out into a flange-like disk-shaped holding member, there may be arranged a membrane contact portion and a further wall portion on the flange-like disk-shaped holding member. This further wall portion may face the first body. With regard to further embodiments, reference is also made to the preceding sections of this document.

In a mounted state, the second body is releasably coupled to the first body. The opening in the second end of the second body faces the first body. In this state, a connection system described herein in some embodiments includes the first body, the membrane, and the second body having an interior space. In addition to the second end, which may be cylindrical, the second body typically includes one or more connections for a fluid carrying system. The second end of the second body includes an interior space, a circumferential wall and an opening. The interior space is typically coupleable to the fluid-carrying system. The circumferential wall includes, on the side facing the first body, a membrane contact portion circumferential around the opening, against which the membrane butts. Also when mounted, the connection system includes a disk-shaped holding member and a connection member. In a mounted state, the disk-shaped holding member may also define a one-piece component with the second end of the second body. Likewise, the holding member may define a distinct component that is releasably connected to the second body. In a mounted state, the connection member is releasably or fixedly connected to the first body and to the disc-shaped holding member. The connection member ensures that the disc-shaped holding member is force-fittingly fixed to the first body. In embodiments where the disc-shaped holding member defines a one-piece component with the second end of the second body, the first and the second body are in this way releasably connected to each other. In embodiments where the disc-shaped holding member defines a distinct component, this is generally connected to the second body, for example, force-fittingly connected, screwed, glued or welded. Also in these cases, therefore, the first and the second body are releasably connected to each other.

Typically, the connection member is designed such that in the fixed state it exerts a contact pressure force on a flange of the first body and a surface area of the disk-shaped holding member facing this flange. The respective surface area of the disk-shaped holding member butts against the flange of the first body. The surface area of the disk-shaped holding member facing the flange of the first body may occupy the entire side of the disk-shaped holding member, which faces the flange. This side has also been referred to in the foregoing as the second side of the disk-shaped holding member. The side of the disc-shaped holding member facing away from the flange of the first body side, in the foregoing already referred to as the first side of the disk-shaped holding member, is generally facing the second body. The disc-shaped holding member furthermore includes a central passage and a peripheral outer edge facing away from the passage. The passage may in some embodiments contain the membrane and be coupled thereto. In some embodiments, the side of the disc-shaped holding member facing the flange, i.e. the second side, is coupled to the membrane. In some embodiments, the side of the disc-shaped holding member facing away from the flange, i.e. the first side, is coupled to the membrane. The circumferential wall of the second end of the second body includes a membrane contacting portion circumferential around the opening thereof. This membrane contact section is also coupled to the membrane. In embodiments where the disc-shaped holding member defines a distinct component, the side of the disc-shaped holding member facing the flange, i.e. the second side, is generally not coupled to the membrane. In embodiments where the disk-shaped holding member defines a terminal structure of the second end of the second body, a side of the disk-shaped holding member facing away from the flange of the first body typically includes an outer surface. Such a side facing away from the flange of the first body of such a disc-shaped holding member is generally not coupled to the membrane.

In some embodiments, where the disc-shaped holding member defines a one-piece component with the second end of the second body, the first body is a fluid-carrying body. In this case, the first fluid-carrying body includes an interior space, and the first end of the first body includes, in addition to a flange, an outlet of the respective interior space, typically an opening. In such embodiments, the second body, namely the second end of the second body, includes an opening, for example a central opening, and the first body includes an opening, for example a central opening. This opening is an opening of the first end of the first body. The opening of the second body is an opening of the interior space of the second end of the second body, which is coupled to the fluid-carrying system. The disc-shaped holding member includes a passage which is, in embodiments in which the disc-shaped holding member defines an integral component with the second end of the second body, identical to the opening of the second body. The opening of the first body may also be an opening of an interior space of the first end of the first body. The interior space of the first end of the first body may also be coupled to a fluid carrying system. In a mounted state the openings of the first body and of the second body are facing each other.

In embodiments where the disc-shaped holding member defines a one-piece component with the second end of the second body, a connection system disclosed herein may already include the first body in a not-yet-mounted state. In this case, the disk-shaped holding member may be coupled to the first body, for example releasably coupled. The disk-shaped holding member may be coupled to the first body in a movable manner. As an example, the opening of the second body may be orientable to the opening of the first body.

The dimensions of the opening of the first body and of the opening of the second body may be designed in such a way that one of the two openings does not exceed the maximum extension of the other opening by more than 10 percent. If, for example, both openings are circular openings, the diameter of one of the two openings may not exceed the diameter of the other opening by more than 10 percent. The dimensions of the opening of the first body and of the opening of the second body may, in some embodiments, be of essentially the same maximum extension, including the same maximum extension. The shapes of the two openings may be matched to one another. For example, the shapes of the two openings may be mirror images of each other. Such matched openings may be aligned with each other such that the outlines of the openings are congruent. In a mounted state, such openings may be congruent with each other. Where both openings are circular openings, the diameters of the two openings may, for example, be essentially the same, including identical diameters.

For better understanding, in the following some embodiments of the connection system will be explained with reference to the figures.

Figure 4:
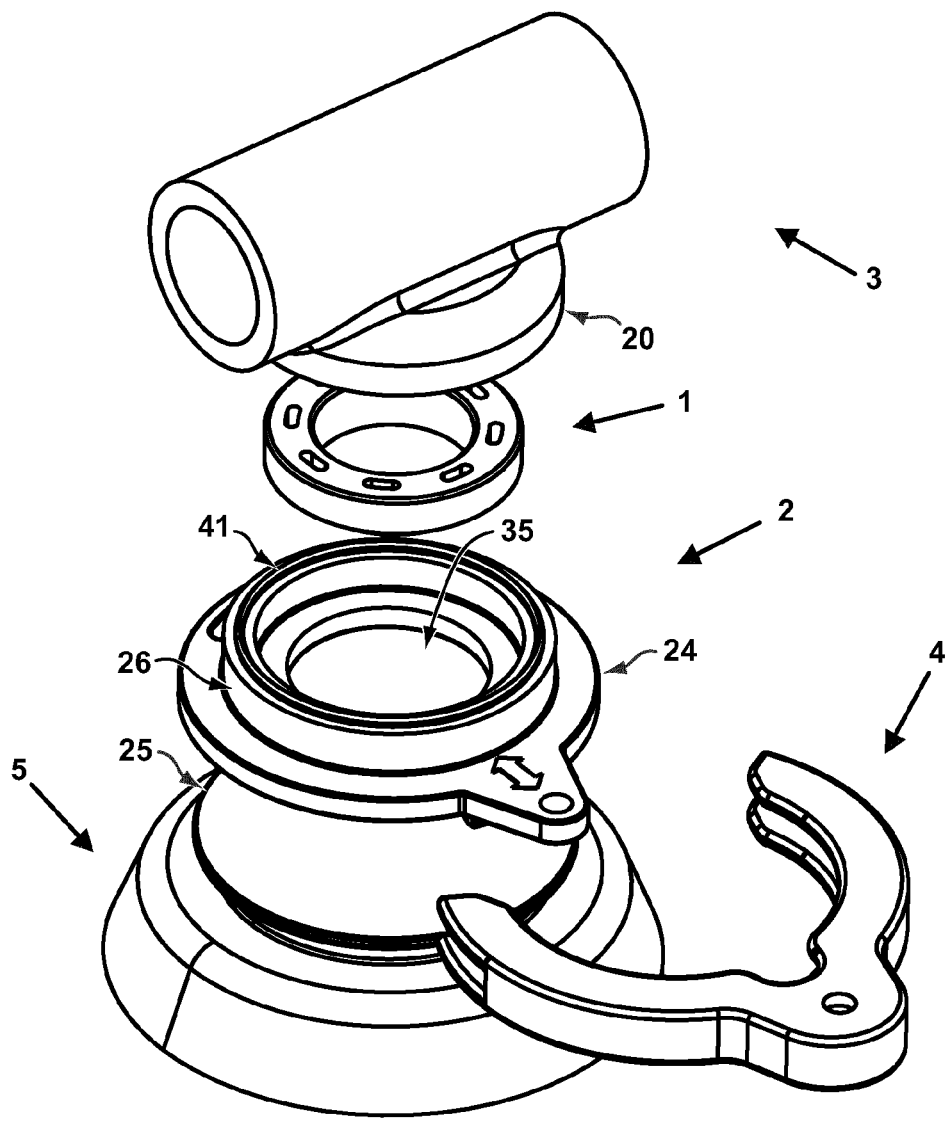
FIG. 4 depicts in exploded view an embodiment of the connecting system with a second body (3), the cylindrical end of which can be seen slanted from above as a wall section (20). The connection member (4) is designed as a semicircular clamp. The figure also shows that the shape of the membrane is designed in such a way that it abuts the circumferential wall (26) of the passage (35) of the disc-shaped holding member (2). A bead (41) of the wall (26) of the disc-shaped holding member (2) contributes to the fixation and sealing of the membrane (1). In this area of the wall (26) a permanent connection, i.e. joining with the second body and/or the membrane, can be made, for example by way of gluing or welding. The flange (25) of the first body (5), the membrane (1) and the disc-shaped holding member (2) define planes that are parallel to each other.

In the embodiment shown in FIG. 4, the connection member (4) is a clamp of semicircular shape, and the disk-shaped holding member (2) is a holding ring. The clamp (4) of semicircular shape presses the holding ring (2) onto the flange of the first body (5). A clamp may be of semicircular shape in the sense of covering about 180° of a circle. A clamp may also be semicircular shape in the sense of covering more than about 180° of a circle, such as for instance about 190° or about 195° of a circle circumference. A design with a circumference of a few degrees above 180° of a circle circumference, such as 185° may be advantageous for providing additional anchoring. Thus, the connection member (4) may be made of a material such as e.g. plastic, which is flexible to a certain extent, so that a respective clamp as the connection member (4) can be bent during assembly. In this way, the clamp can be stretched apart to a certain extent. A clamp, which encompasses a few degrees more than 180° of a circle circumference, may thus be slid over the disc-shaped holding member (2). It then latches over the disc-shaped holding member and returns to its previous shape, in which it encompasses more than 180° of the circumference of the disc-shaped holding member.

Figure 8:
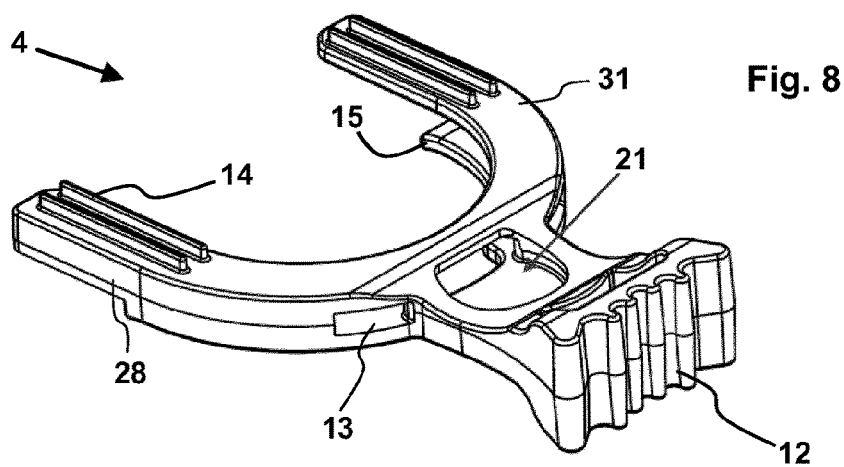
FIG. 8 depicts a further embodiment of the connection member (4) in the form of a U-shaped clamp with a gripping element (16) and two legs (31). The perspective chosen is again slanted from above, i.e. from the direction of the second body (3). The legs include a side wall (28) with a recess (13) in the form of an opening. The range of the connection member, in which the legs (31) meet, is continuous, so that in this embodiment no provision is made for a recess. In this embodiment, in the range of the handle element (12) there is a passage through a plane that is parallel to the plane defined by the flange of the first body (5), cf. e.g.
Figure 9:
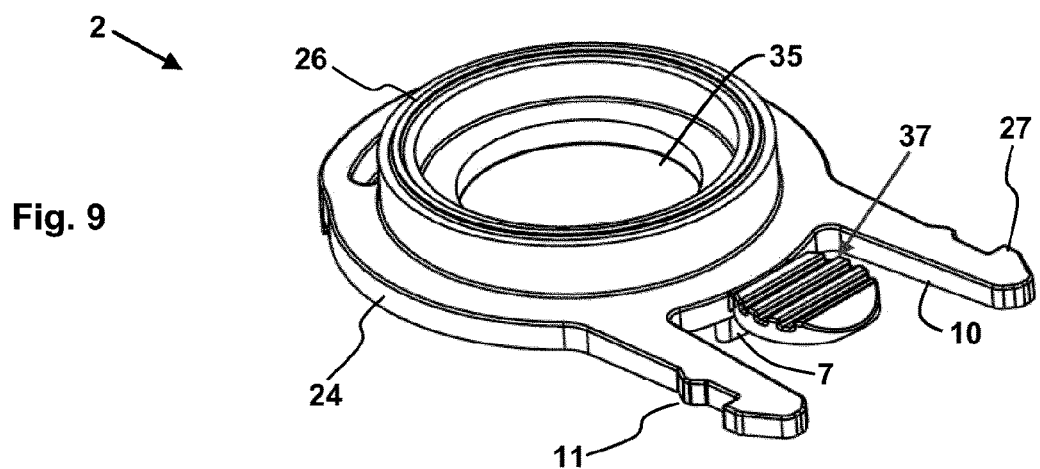
FIG. 9 depicts a further embodiment of the disc-shaped holding member (2) with two arms (10), slanted from above, i.e. from the direction of the second body (3). Again, the peripheral outer edge (24) of the holding member defines a wall. In the range between the two arms (10) there is an insertion element (37), which emanates elastically from the outer wall (24). The shape of the insertion element (37) is matched to the shape of the through opening (21) of the connection member (4) depicted in FIG. 8.
Figure 10A:
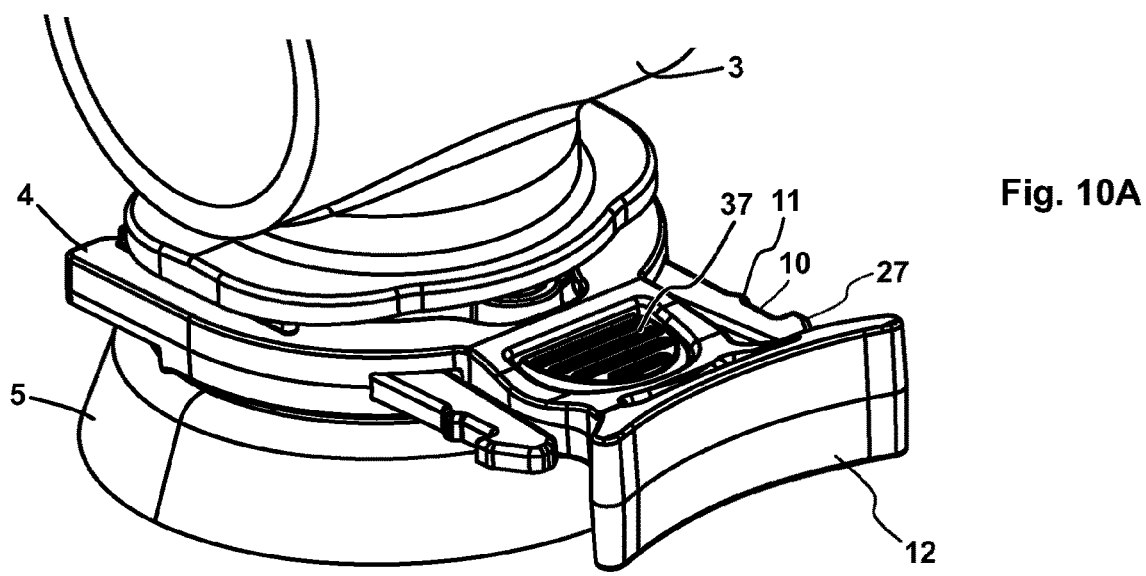
FIG. 10A. In this case the connection member has a through opening (21) through this plane.
Figure 10B:
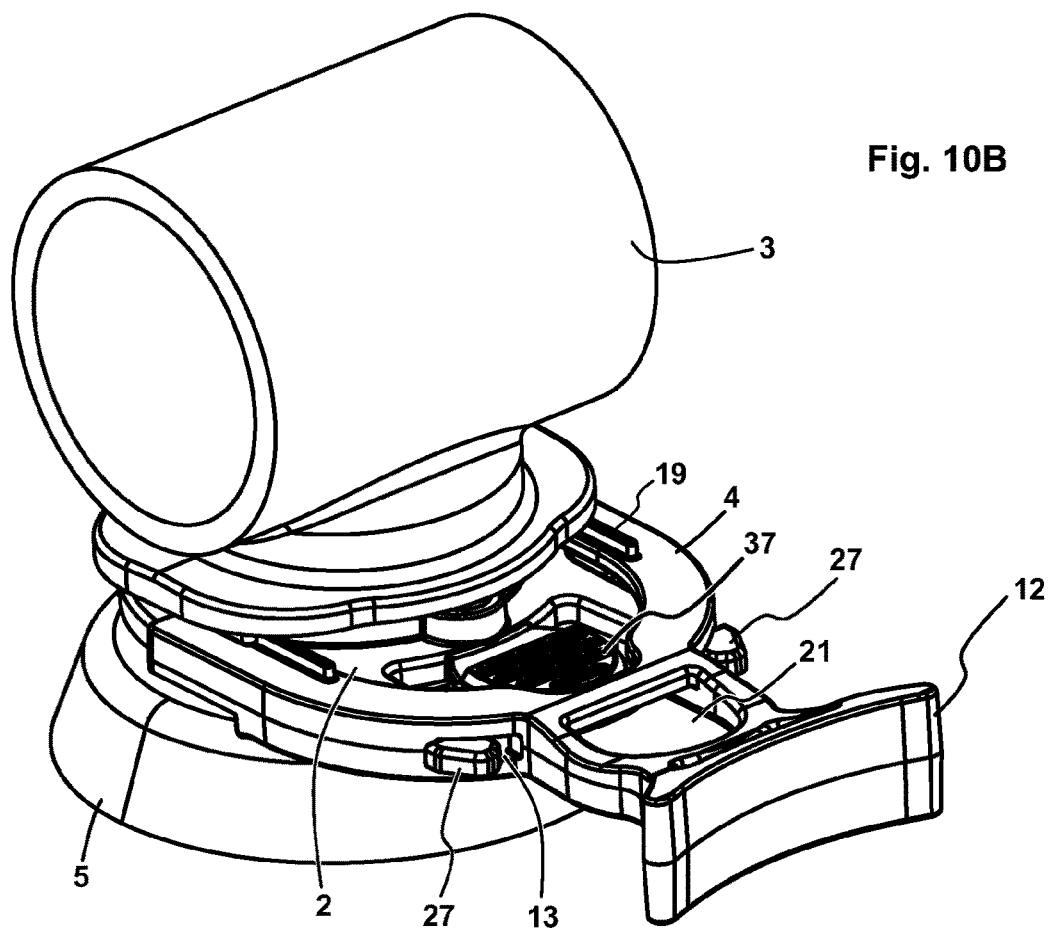
FIG. 10B depicts the connection system shown in FIG. 10A in the open position. Relative to the viewer, the connection member (4) is shifted forward, so that the insertion element (37) of the disc-shaped holding member (2) and the recess (21) of the connection member (4) are arranged offset from one another. The connection member (4), inter alia in contrast to the embodiment of FIG. 8, contains only one bar (19) instead of two bars (14).
Figure 10C:
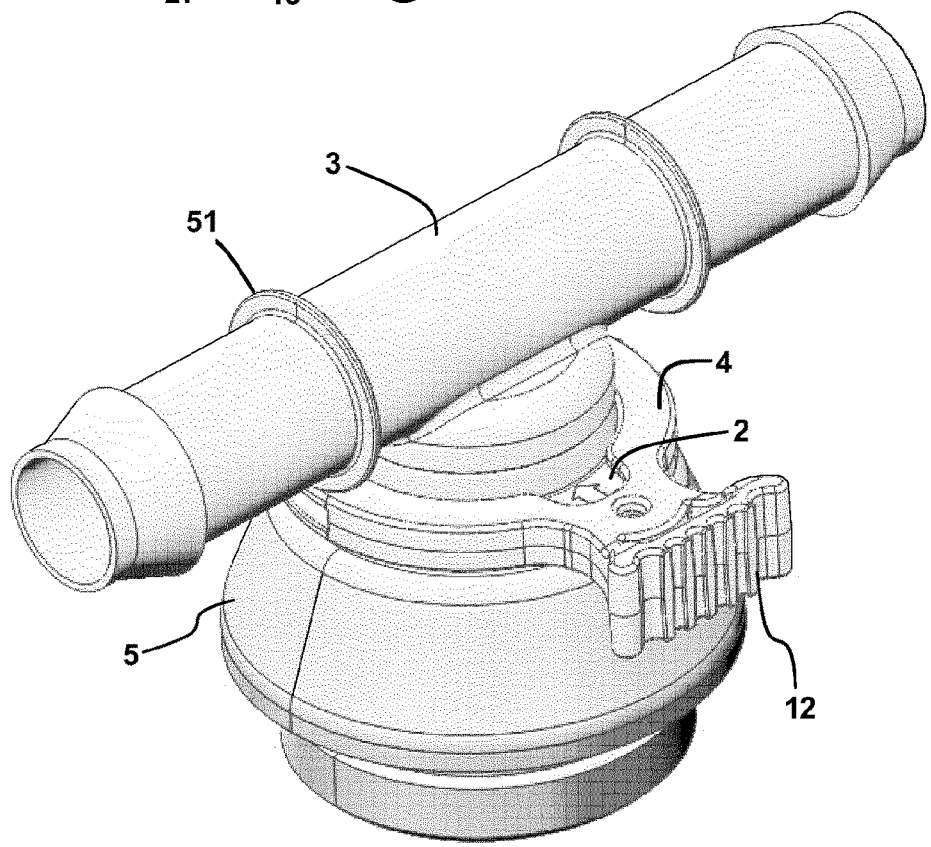
FIG. 10C depicts a further embodiment of the connection system in which the disk-shaped holding member (2) does not include arms and the connection member (4) does not include bars (14), cf. e.g.
Figure 10D:
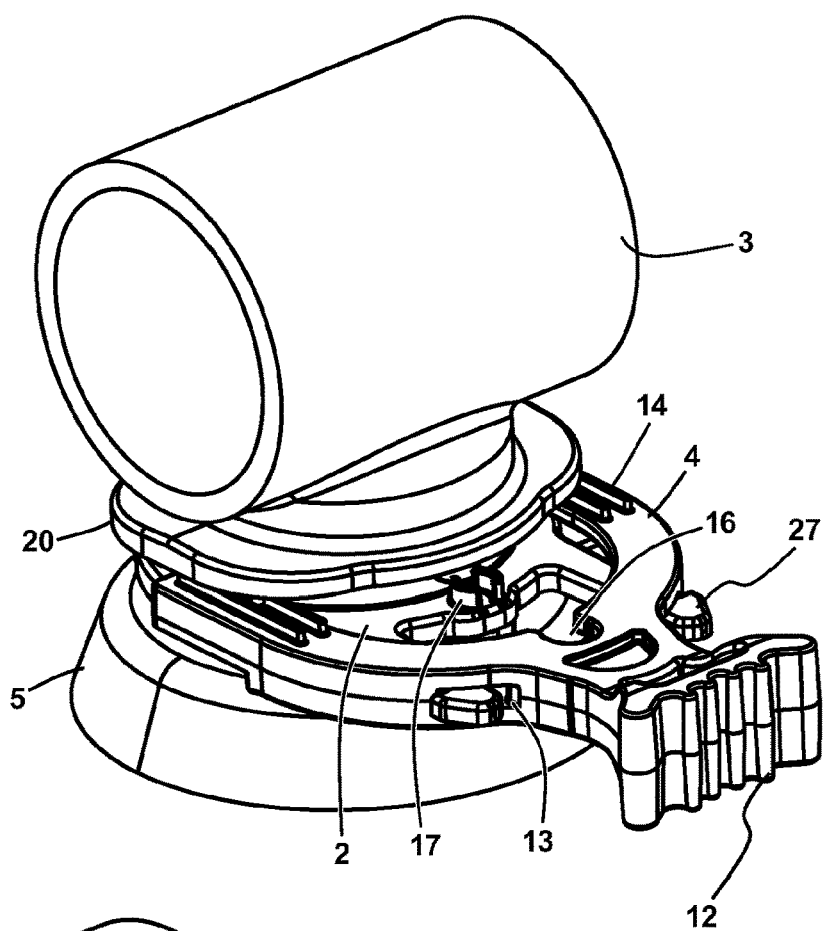
FIG. 10D depicts an embodiment of a connection system, in which the embodiment of the disk-shaped holding member (2) depicted in FIG. 6 is arranged between the first body (5) and the second body (3). The embodiment of the connection member (4) depicted in FIGS. 5A and 5B is already partly positioned between the first body (5) and the second body (3) in such a way that a lock can be achieved by pressing the handle element (12). The bars (14) on the connection member (4) define a bidirectional guide at the wall portion (20) of the second body (3). The connection member (4) and thereby the entire connection system is thus in an open state in which it does essentially not grip around the peripheral outer edge of the disc-shaped holding member (2) and the flange (25) of the first body (5). The clamping element (17) of the disc-shaped holding member (2) and the recess (16) of the connection member (4) are arranged offset from each other. The bars (14) on the connection member (4) are exposed to guidance by pins shown in FIG. 7. Hooks (27) can be seen at the legs of the disc-shaped holding member (2), which rest in recesses (13) of the connection member (4). By pressing the handle element (12), the connection member (4) can be shifted, whereby the legs of the disc-shaped holding member (2) move through the respective recess (13).
Figure 10E:
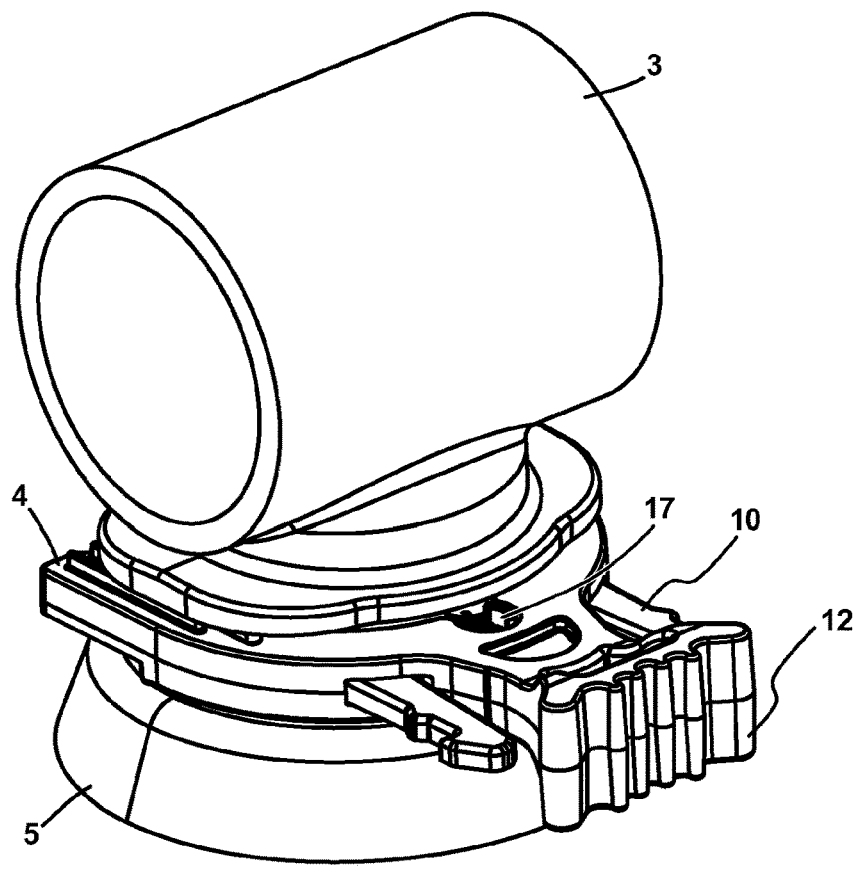
FIG. 10E depicts the embodiment of the connection system shown in FIG. 10D in a closed state. The clamping element (17) of the disc-shaped holding member (2) is slid into the recess (16) of the connection member (4) and locked in in place therein. The connection member (4) grips around a peripheral outer wall of the holding member (2), which is hidden from view in this perspective, as well as around the flange of the first body (5) that is likewise hidden from view.

For example, in the embodiments depicted in FIG. 10A and FIG. 10E, the connection member (4) is a U-shaped clamp with arms (31), and the disc-shaped holding member (2) is a holding ring with legs (10). FIGS. 5 to 6, 8 and 9 depict further embodiments of a connection member with a U-shaped clamp, which allow simple mounting with guides so that, where applicable, it can also be mounted without visual contact or without viewing the connection system. Furthermore, these embodiments illustrate the possibilities for pre-assembly of the connection member (4), which also allows mounting the connecting system with just one hand, see e. g. FIG. 10 and FIG. 12.

Figure 5A:
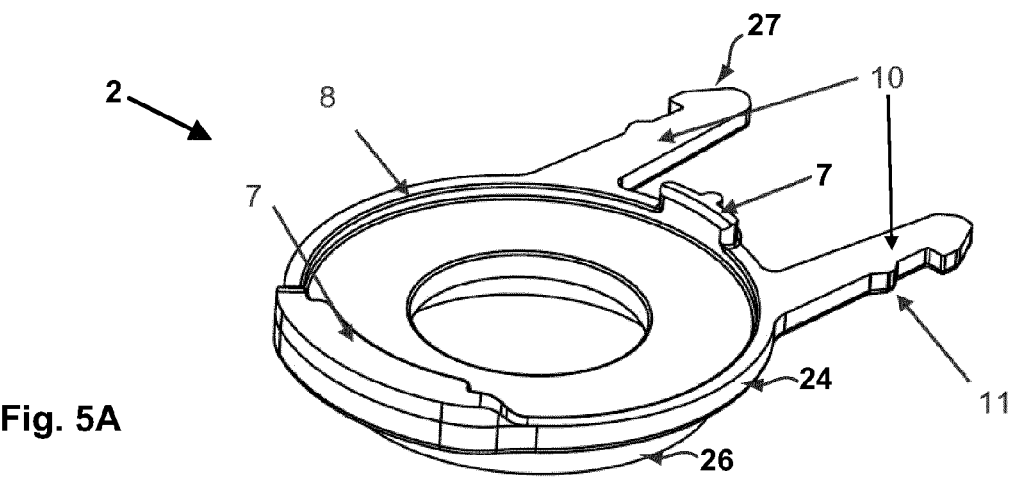
FIG. 5A depicts, slanted from below, an embodiment of the disc-shaped holding member (2), i.e. from the direction of the first body (5). The disc-shaped holding member is designed as a holding ring with two arms (10). A guide edge (8) continues into the two arms (10). The arms (10) include noses (11) and hooks (27). The guide edge (8) furthermore continues in two opposing hook members (7).
Figure 5B:
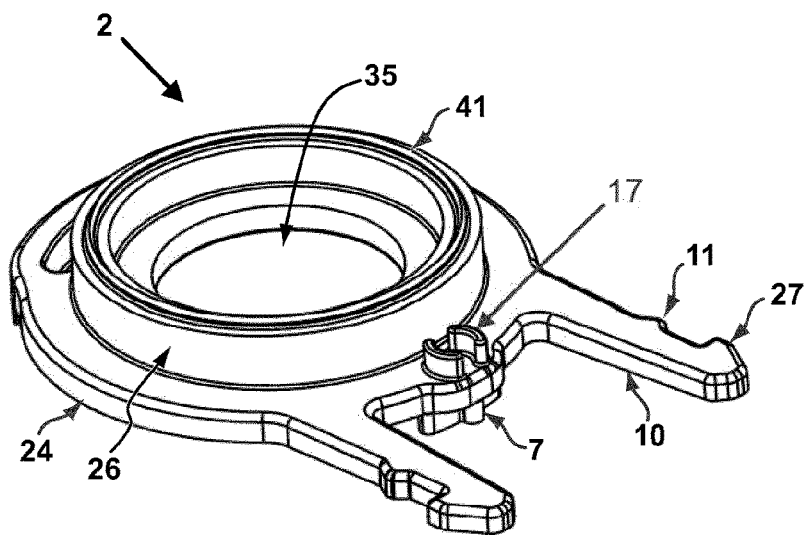
FIG. 5B depicts, slanted from above, i.e. from the direction of the second body (3), the embodiment of the disk-shaped holding member (2) with a passage (35), which is shown in FIG. 5A. The peripheral outer edge (24) of the holding member defines a wall. From the peripheral outer wall (24) there project two arms (10), each having a nose (11) and a hook (27). On the side facing the second body (3) there is a circumferential wall (26) with a bead (41). In the area between the two arms (10), there can be seen one of the hook members (7) arranged on the side facing away from the second body (3). On the opposite side, facing the second body (3), a clamping element (17) is arranged, which can is insertable into the recess (16) of the connection member (4).
Figure 6:
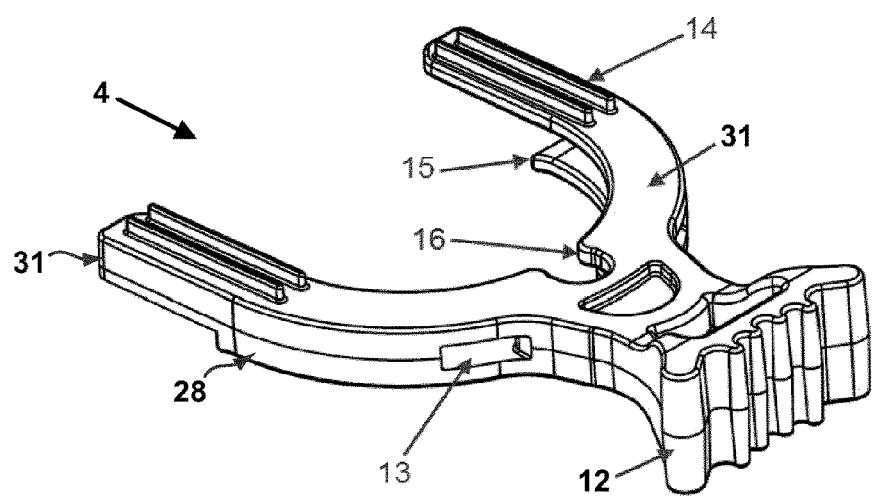
FIG. 6 depicts an embodiment of the connection member (4) in the form of a U-shaped clamp with a handle element (12) and two legs (31), slanted from above, i.e. from the direction of the second body (3). The legs include a side wall (28) with a recess (13). On the side facing the second body, there are located bars (14), and in the area of the connection member, in which the legs (31) meet, there is provided a recess (16). An infeed edge (15) is arranged on the side of the legs (31) opposite the bars (14), i.e. the side facing the first body (5).
Figure 7:
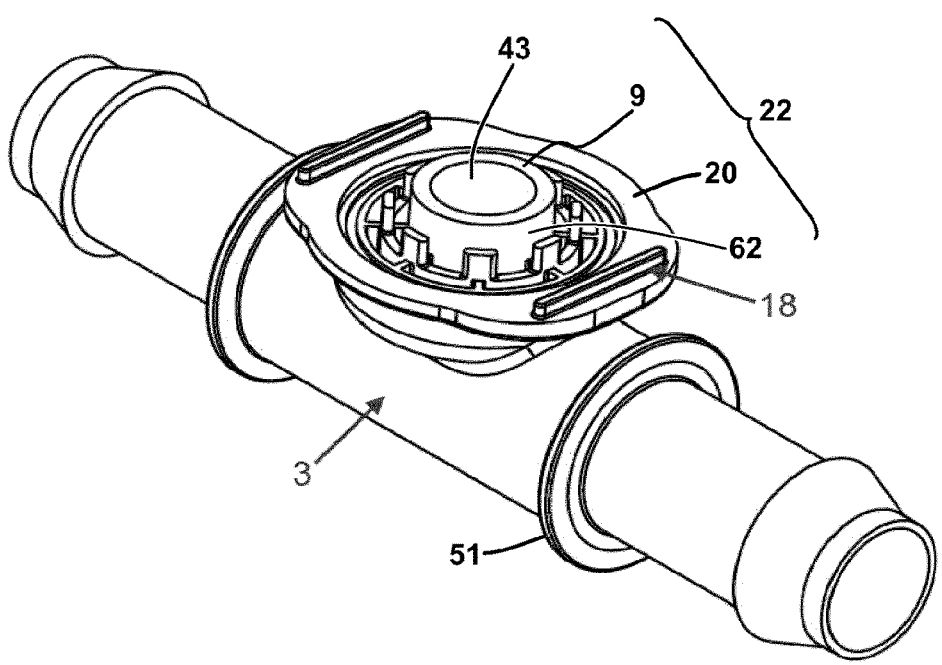
FIG. 7 depicts an embodiment of the second body (3) in the form of a measuring chamber with two annular collars (51) slanted from below, that is from the direction of the disk-shaped holding member (2). Visible are thus the wall portion (20) with the opening (43) of the second body (3), and the circumferential membrane contact portion (9) e on the circumferential bead (62). Guide bars (18) are arranged on the side of the peripheral wall (22) on which the disk-shaped holding member (2) abuts.

The disk-shaped holding member (2) may, e.g. in embodiments of FIG. 5, be oriented over the first body (5) in such a way that the passage (35) of disc-shaped holding member (2) is located over the flange (25) of the first body (5), cf. FIG. 6. The guide edge b) and the hook elements (7) of the holding member (2) face in the direction of the flange (25). On the flange (25) of the first body (5), the disk-shaped holding member (2) may then be hooked by a slight tilting movement with the larger of the two hook elements (7), and be tilted onto the one of the first body (5).

In the same way, a disk-shaped holding member (2), which has already been connected to the second body (3) in advance, is couplable to the first body (5). The first body is also fixable to the second body. With the membrane (1) inserted, the disk-shaped holding member (2) can be placed on the second body (3) in such a way that the wall (26) of the holding member (2) butts against the recess (28) as a retrace of the second body (3). For this purpose, previously the membrane (1) may have been slid onto the circumferential wall (22) of the second body (3), and the wall (26) of the holding member (2) may have been slid onto the membrane (1), so that the membrane (1) separates interior space (23) of the cylinder from the ambience. The first body (5) can be oriented below the disc-shaped holding member (2), connected to the second body (3), in such a way that the flange faces the guide edge (8) and the hook elements (7) of the holding member (2). The flange can be hooked into the larger of the two hook elements (7) of the holding member (2), and tilted onto the holding member (2), and thus onto the second body (3), by a slight tilting movement. Such a tilt mounting is advantageous over a sliding mounting, since in this way there is no friction generated between the membrane (1) and the first body (5). There is thus no risk of damage or impact on the mechanical properties, for example of a membrane/measuring element connection, if the first body (5) includes or defines a measuring element.

Figure 17A:
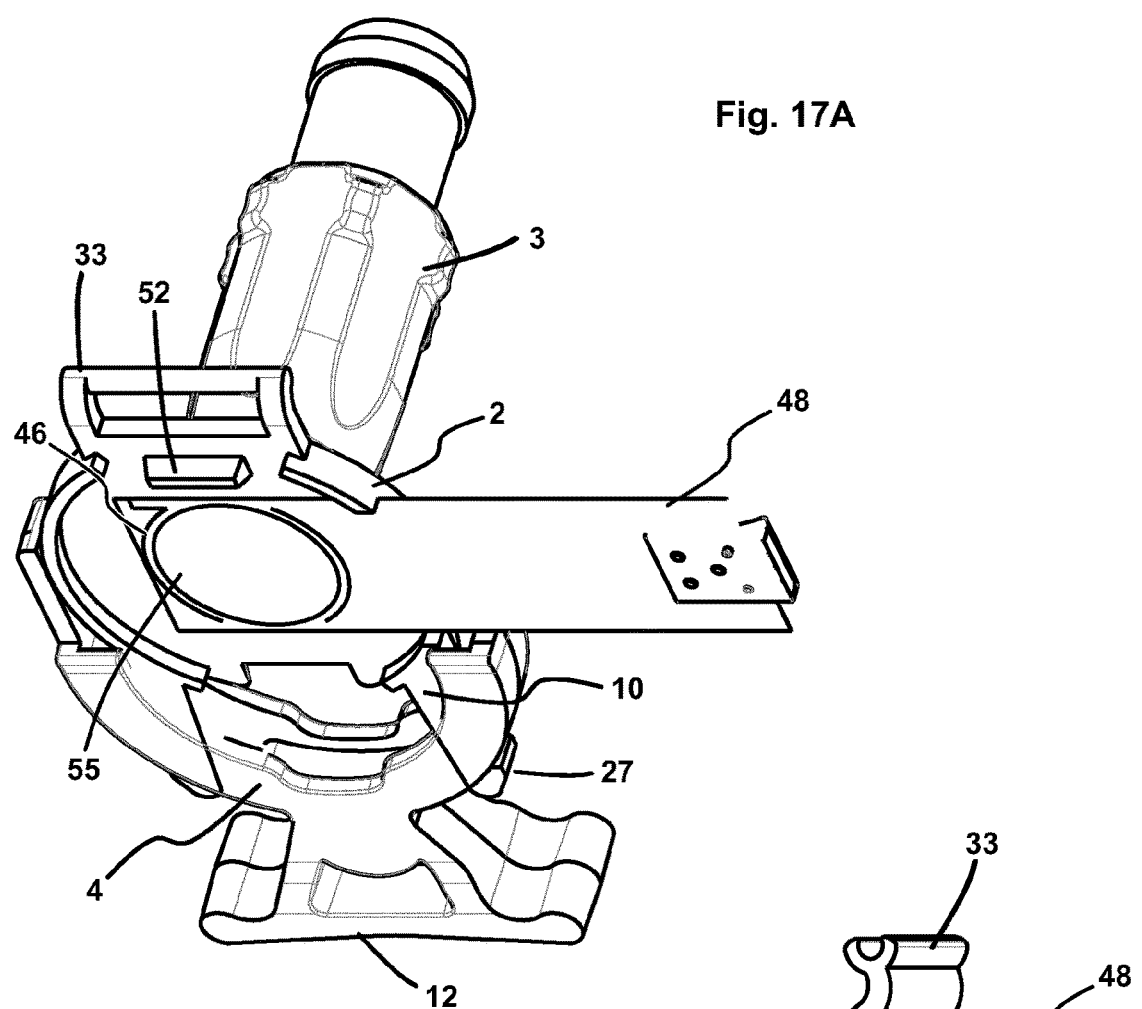
FIGS. 17A and 17B depict a connection system for releasably force-fittingly coupling a first fluid-carrying body (5) shown in FIG. 17B to a second fluid-carrying body (3) shown in FIG. 17A. The first and the second body are movably connected by a hinge (33). The opening of the interior space of the first body (5) and the central opening (55) of the interior space of the second body (3) are each covered by a releasable protective film (48). The releasable protective film (48), which closes the interior space of the second fluid-carrying body (3), rests on a circumferential protrusion (46), see FIG. 17A. The first body (5) includes a first cylindrical end with a flange (25). The second body (3) includes a second cylindrical end which continues into a flange-like disk-shaped holding member (2) with a guide edge (52) and two legs (10). At the disk-shaped holding member (2) there is arranged a connection member (4) with a handle element (12). Two arms with hooks (27) emanate from the peripheral outer wall of the holding member (2) which are slidable in or through corresponding recesses or passages of the connection member (4).

In some embodiments, the disc-shaped holding member (2) includes an element that can facilitate assembly of the user. This helps to reliably ensure avoiding damage to the holding member and to the connection member. Thus, the disc-shaped holding member (2) can include an element that prevents misalignment during mounting. In this regard, FIG. 3 and FIG. 5A show a peripheral guide edge (8). Other components of the connection system such as e.g. the releasable connection member or, where applicable, the second body may have precision-fitting elements that can contact a corresponding element of the disk-shaped holding member (2). The circumferential guide edge (8) shown in FIG. 3 and FIG. 5A has a design adapted to the flange of the first body (5), which facilitates mounting the disk-shaped holding member (2) onto the first body (5). Via contacting matching elements to each other, according to the key-keyhole principle or the principle of the Poka Yoke, unintentional errors can be prevented from causing damage, for example during movements or when aligning components. In this way, it is possible to provide additional support. As a further example in this regard, FIG. 17A shows a conical guide bar (52), which can achieve locking in place upon mating the flange-like disc-shaped holding member (2) with the flange (25) of the first body. The first body (5) may include an element that is geometrically adapted for contacting the conical guide bar (52) and thereby achieving self-locking. In this way, arranging the first and the second body offset to one another can be prevented, when they are brought together.

A circumferential guide edge (8) and a second, typically smaller, hook element (7) allow a simple, secure and defined positioning of, for example, a measuring chamber on a measuring element. The second hook element (7) may be taken to be a guide segment. In particular, defined positioning of the membrane on the force sensor (e.g. piezo element) of the measuring element is ensured, which is important for the transmission of force.

In some embodiments, the connection member (4) includes pairs of opposing walls, protrusions—including legs—or recesses. The opposing walls or protrusions of a pair of walls or protrusions may have a resilience against each other, which allows mounting areas of the disk-shaped holding member (2). As an example, the connection member (4) may include two pairs of legs arranged one above the other, each pair of legs defining one half of a U-shaped clamp. The two legs of such a pair of legs may be designed in such a way that arms of the disc-shaped holding member (2) can be slid between the legs of a pair of legs of the U-shaped clamp. This process of insertion may require resilience of the legs of the connection member.

In some embodiments, the connection member (4) is designed as a U-shaped clamp, the U-shape being defined by two legs (31), which may also be referred to as a pair of legs. In this case, the two legs abut against opposite sides of the disc-shaped holding member (2), typically on opposite sides of the peripheral outer edge thereof. Such an embodiment is inter alia shown in FIG. 6. In this embodiment, each leg (31) of the connection member (4) includes a side wall (28). The two side walls (28) abut against respective opposing sides of a peripheral outer edge (24) of the holding member (2). The side walls (28) of the two legs (31) allow gripping around both the disc-shaped holding member (2) and the flange (25). An infeed edge (15), which can be both concave or convex, facilitates mounting on the first body (5).

The disc-shaped holding member (2) and/or the connection member (4) may include features that allow moving the connection member (4) relative to the holding member (2) in an at least partially controlled manner. Respective features can set a guide for a movement of the connection member (4) similar to a rail. A combination of one or more protrusions—including legs—on the disc-shaped holding member (2) and one or more recesses of the connection member (4) may for instance serve this purpose. Similarly, a combination of one or more protrusions on the connection member (4) and one or more recesses of the disk-shaped holding member (2) may be provided. As an example, the connection member (4) may include a circumferential wall which is circumferential around at least one segment of the circumference of the connection member (4). Depending on the shape of the connection member, the circumferential wall may include a uniform or non-uniform thickness. Typically, the shape of this circumferential wall is adapted to the shape of the peripheral outer edge of the disc-shaped holding member (2) in such a way that one or more contact surfaces of connection member (4) and the disc-shaped holding member (2) can abut one another. In some embodiments, a form-locking connection of the disc-shaped holding member (2) and the connection member (4) can be achieved. The circumferential wall of the connection member (4) may have the shape of a semicircle or a semi-oval. The circumferential wall of the connection member (4) may also be V-shaped, U-shaped or M-shaped. The peripheral wall of the connection member may, in some embodiments, have the shape of an open rectangle or an open square. FIGS. 6 and 8 show embodiments in which a circumferential wall (28) of the connection member (4) is U-shaped.

In the embodiments shown in FIGS. 6 and 8, the circumferential wall (28) of the connection member (4) has a plurality, in this case two, axially offset recesses. The dimensions of the recesses (13) allow accommodating arms (10) of a disc-shaped holding member (2). The dimensions of such recesses may also allow providing two different positions for protrusions such as arms (10) of a disc-shaped holding member (2). By way of example, correspondingly axially offset protrusions of the disk-shaped holding member (2) in the form of a bayonet closure may be held in recesses (13) of the connection member (4). The circumferential wall (28) may for example also include a pair of recesses axially opposing each other or three axially offset recesses. The shape of the recesses may be selected in such a way that the protrusions of the disc-shaped holding member (2) are fixable in the form of a bayonet closure by a rotational movement of the connection member (4).

To support and/or facilitate a movement of the connection member (4) relative to the disk-shaped holding member (2), a gripping element (12) may be provided. In the embodiments shown in FIGS. 6 and 8, a gripping element (12) is arranged between the recesses (13).

The disk-shaped holding member (2), which may, for example, include two arms (10), may include a protrusion (11) as a locking means, through which the holding member (2) in the connection member (4), which may for example have the shape of a clamp, can be held in a mounting position. Thus, a pre-assembly of the holding member (2) and the connection member (4) is possible. Thereby it is possible to move the connection member (4) on the disk-shaped holding member (2) by a thumb movement at the gripping element (12), without releasing the clamp of the connection member (4) from the holding member (2). With a thumb movement, the connection member (4) can be moved at the handle element (12) over the disc-shaped holding member (2) and the flange (25) of the first body, so that both are firmly pressed together.

After use (or in the case of incorrect assembly), a gripping element (12) of the connection member (4), as shown in FIGS. 6, 8, 10 to 12, may also serve in separating the connection, the clamp-shaped connection member (4) being pulled from the disc-shaped holding member (2) again. For safety, a defined end position of the connection member (4) on the holding member (2) may be indicated. Furthermore, a clamping (17), for example in the form of a bar, including a pair of bars, may be used to secure the mounting position. A pair of bars, for example in a configuration corresponding to the shape of circular segments, may in one embodiment in a final position be clamped in a matching recess (16) of a connection member (4). In this way, a defined clamping and thereby operational safety can be ensured.

This type of connection mechanism, e.g. clamping mechanism, involves an intermediate position, in which the holding member (2) and the connection member (4) are already connected, but no compression with the first body (5) has yet occurred. This allows mobility, including rotability, of the first body on the second body. This facilitates for example mounting a measuring chamber with the hoses that are typically connected thereto, as well as aligning the hoses. Once fully aligned, the clamping can then be pushed into the defined end position and locked.

As another example, the disk-shaped holding member (2), may include an insertion member (37) as shown in FIG. 9, which may be arranged between, for example, arms (1) of the holding member (2), as in the embodiment shown. The connection member (4) may include a recess such as a through opening (21), which can accommodate the insertion element (37), see FIG. 8. The insertion element (37) may be flexible to such an extent that the connection member (4) can be slid over the insertion element, if applicable. As shown in FIG. 10, the connection member (4) may be locked in place in this way in a closed state. FIG. 10B shows an open state in which the connection member (4) takes a position that is shifted diagonally forward toward the viewer. By pressing on the handle element (12) of the connection member (4), the connection member (4) may be moved diagonally backward from the direction of the viewer. FIG. 10A shows a closed state in which the insertion element (37) is held in the recess (21) of the connection member (4).

There may also be a protrusion, a bar or something similar provided on the disc-shaped holding member (2), facing in the direction of the second body. A respective cut-out, recess or groove on the connection member (4) may be designed in such a way that it can accommodate the protrusion, bar etc. on the disc-shaped holding member (2). FIG. 5 shows a clamping (17) arranged on the disc-shaped holding member (2). A recess as a cut-out (16) on the connection member (4), adapted to the dimensions, is shown in FIG. 6. FIGS. 10D and 10E show the open state of a respective connection system, as well as the interlocking of the elements (17) and (16) in the closed state (FIG. 10E).

Figure 11D:
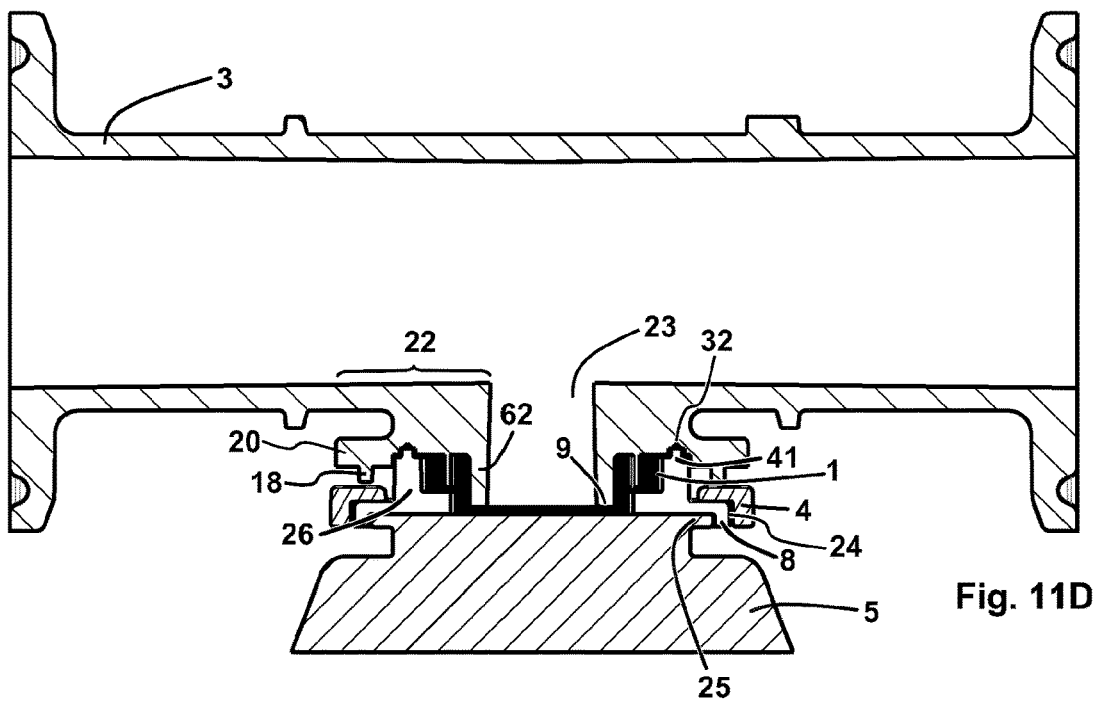
FIG. 11D depicts to scale the embodiment of the connection system that is schematically reproduced in FIG. 11A. The connection member (4) is provided in an embodiment as a U-shaped clamp, and is in an open position, in which the U-shaped clamp is essentially released from the circumferential portion of the disc-shaped holding member (2) (cf.
Figure 11E:
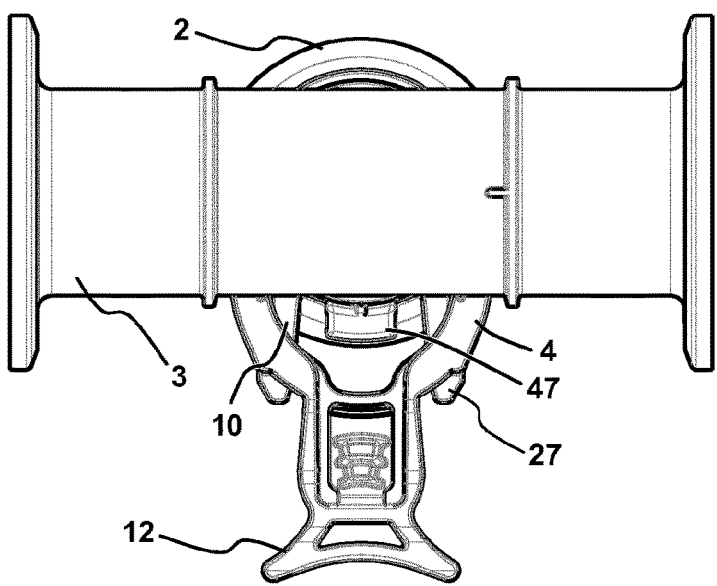
FIG. 11E depicts the embodiment shown in FIGS. 11A to D and F in an open position, cf.
Figure 11F:
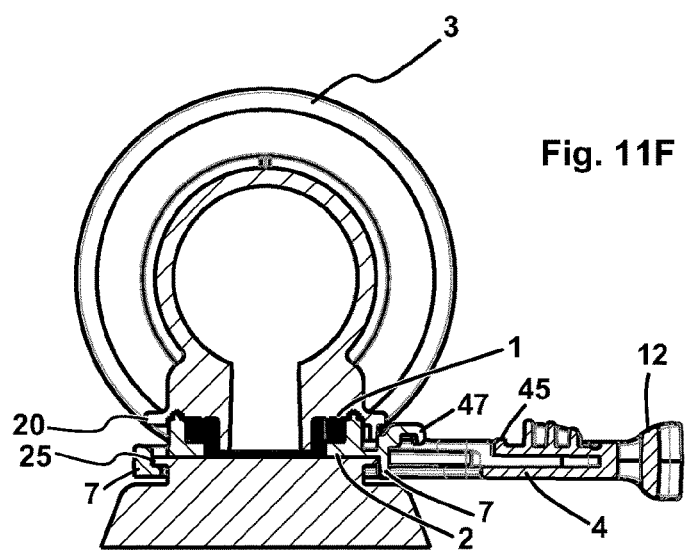
FIG. 11F depicts the embodiment shown in FIGS. 11A to E in an open position. Compared to FIG. 11C, the connection member (4), in an embodiment of a U-shaped clamp, is shifted to the right from the viewer's perspective. The bail (47) of the disk-shaped holding member (2) and the holder (45) of the connection member (4) are arranged offset from one another. Due to the perspective, the connection member (4) in the shown cross-section does still not grip around the flange (25), since such gripping around can only occur on the side facing the viewer and the side facing away from the viewer. Instead, hook elements (7) of the disc-shaped holding member (2) are recognizable.
Figure 12A:
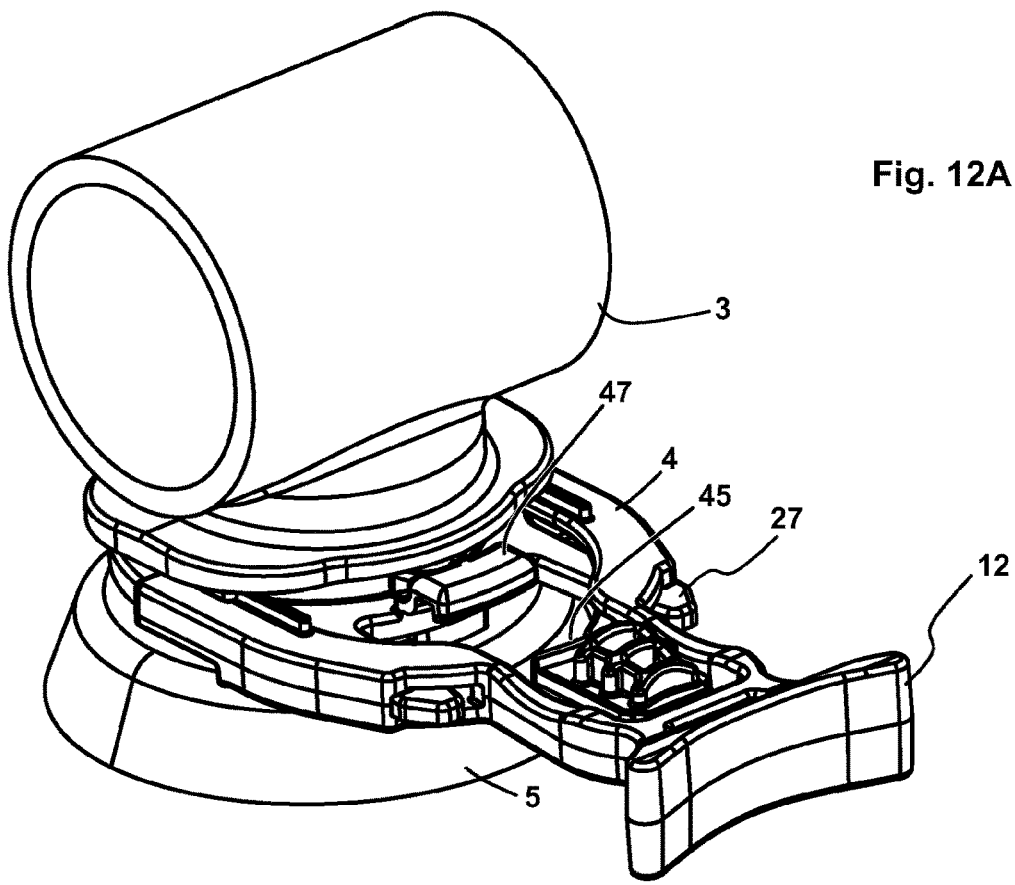
FIGS. 12A and 12B depict in perspective view the embodiment of the connection system shown in FIG. 11 in an open (A) and a closed (B) position. In the open position, the hooks (27) of the disc-shaped holding member (2) retain the arms (10) in the recesses (13), and prevent a complete separation of the connection member (4) and the disc-shaped holding member (2). In the closed position, the bail (47) of the disk-shaped holding member (2) retains the holder (45) of the connection member (4), and prevents the connection member (4) and the holding member (2) from being displaced against each other.
Figure 12B:
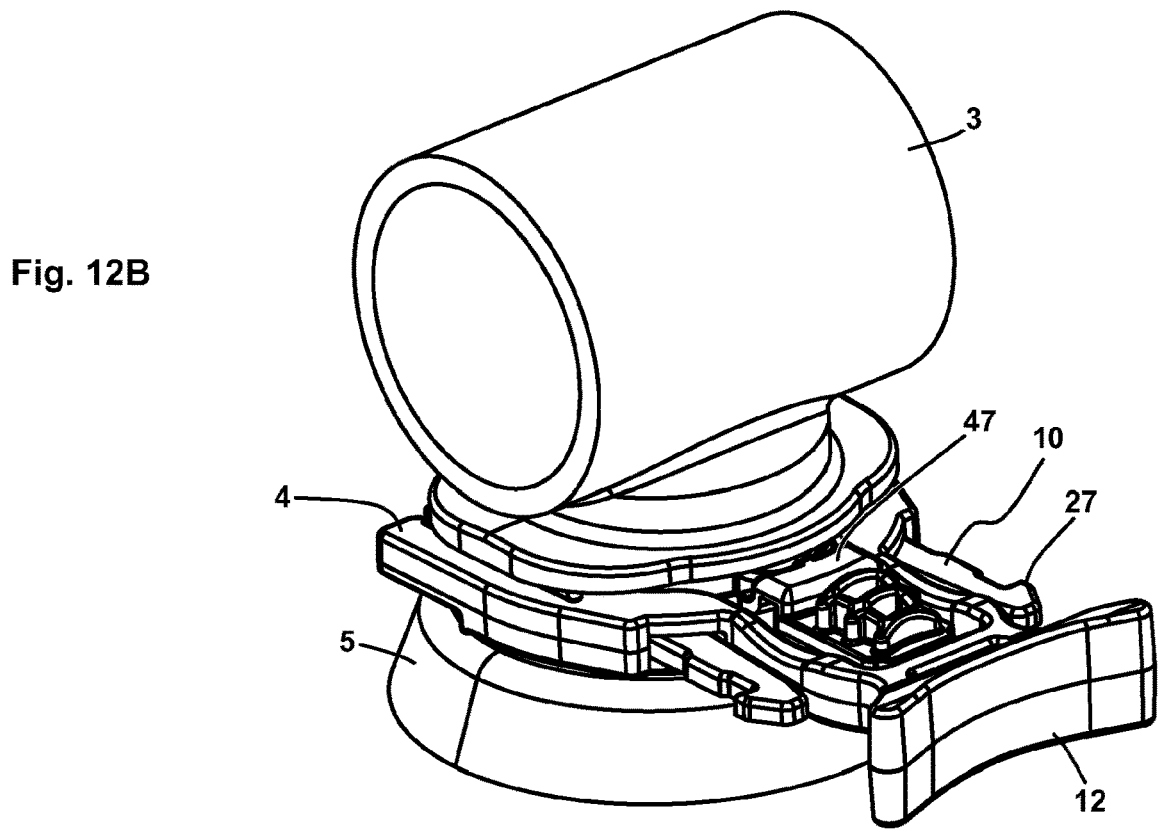

As a further example, FIG. 11B, FIG. 11C, FIG. 11F and FIG. 12 show a bail (47) arranged on the disk-shaped holding member (2). There may be a holder (45), for example designed as a bar, provided on the connection member (4), as shown in FIG. 11C, FIG. 11F and FIG. 12. The bail (47) may be designed in such a way that it is capable of at least partially envelop and thus lock the holder (45) in place. In this case, the bail (47) may be flexible to such an extent that it is possible to slide the holder (45) under the bail (47). FIG. 12A shows a respective connection system in an open state, in which the connection member (4) can be pushed diagonally backwards away from the observer by pressing on the handle element (12) of the connection member (4). The corresponding closed state, in which the bail (47) partially grips around the holder (45), is shown in FIG. 12B.

Figure 13:
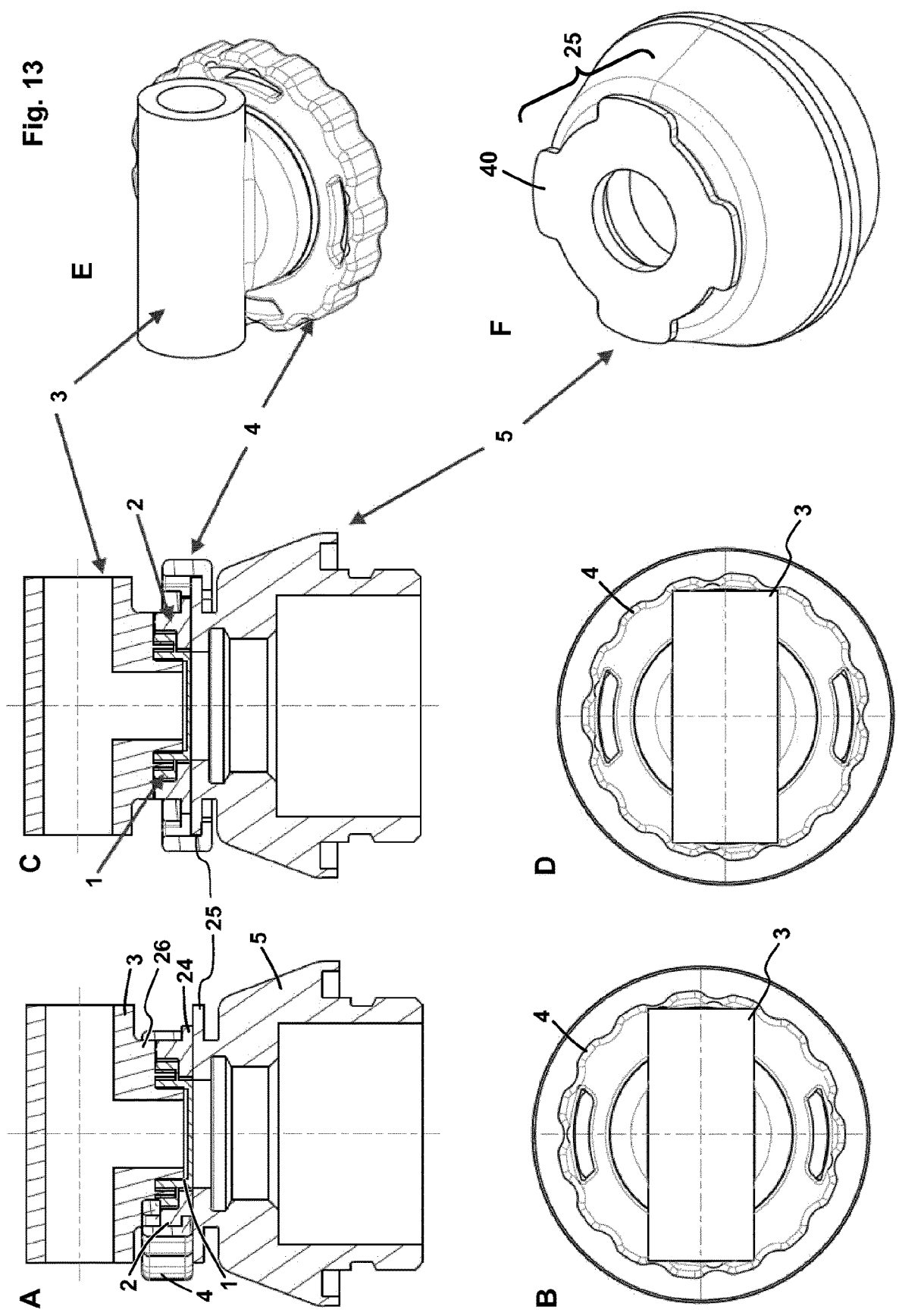
FIGS. 13A-13F depict an embodiment of the connection system, in which the connection member (4) defines a segmented locking ring.

In the embodiment shown in FIG. 13, locking is achieved by turning the connection member (4), which has the shape of a mounting ring. The underlying mechanism may be taken to be a variant of a bayonet lock. Here, pressing is ensured by rotating the mounting ring (4), optionally with undercut elements, via the flange (25) of the first body (5). Also in this embodiment, single-handed mounting is possible.

Figure 14A:
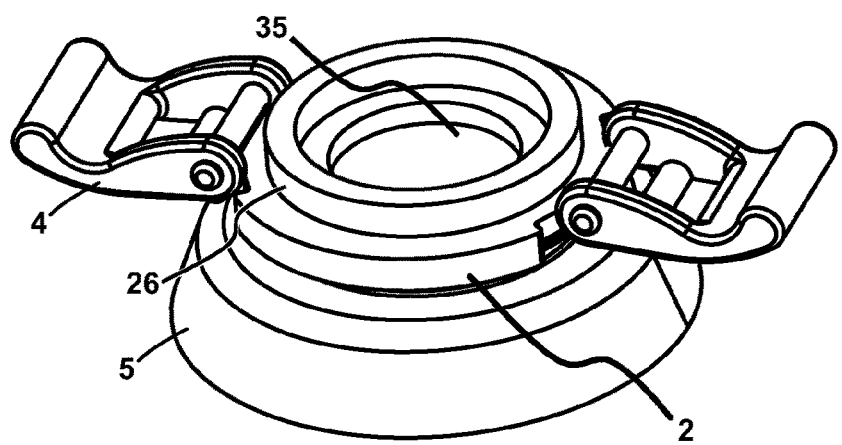
Figure 14B:
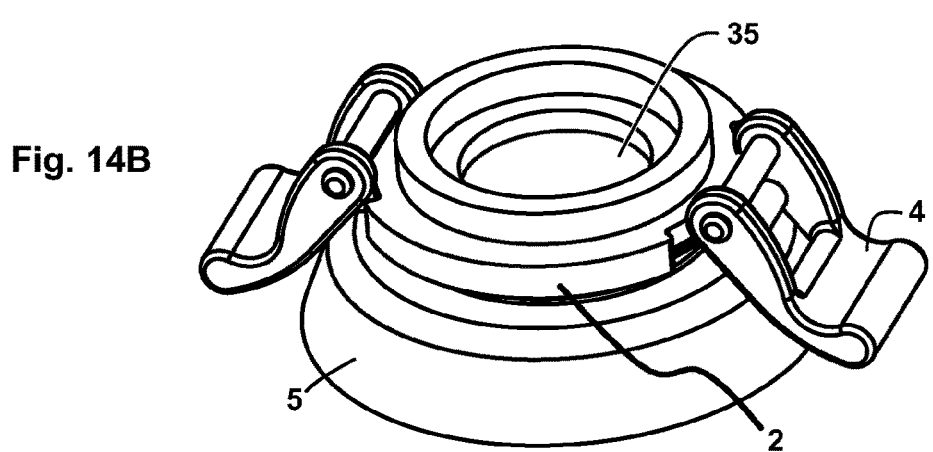
Figure 14C:
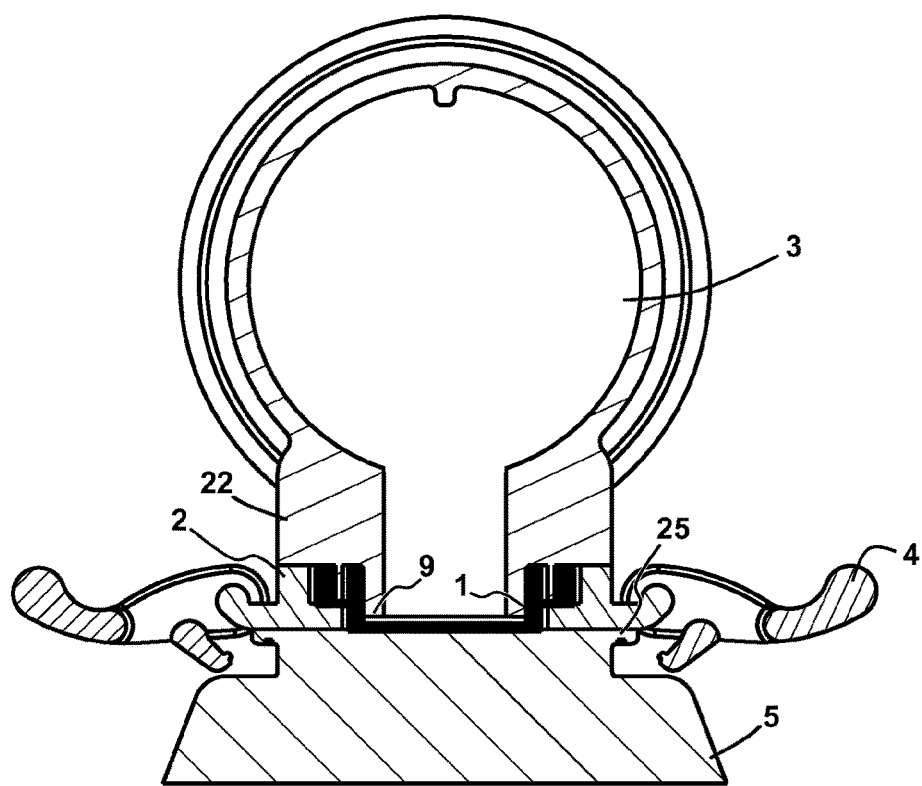

FIG. 14 shows a compression by two clamping levers as a connection member (4). One or more further clamping levers may be provided. Again, single-handed mounting is possible.

FIG. 16 shows an embodiment in which the connection member (4) includes a pivotable arm (30) and a rivet-shaped protrusion (42). As shown in the figure, the pivoting arm may include an element which is geometrically adapted to be releasably fixed in the rivet-shaped protrusion (42). This may for example be a ribbing, one or more pins, one or more ribs or one or more bars. Such geometric elements, which may serve as a toothing, may be provided on an extension of the arm, such as a tongue (49) or a band. The rivet-shaped protrusion (42) may include a geometric element that is adapted to contact the geometrical element provided on the pivotable arm (30). Engaging or latching can be achieved in a way similar to a cable connector. For example, a wedge or a mandrel may be arranged in the rivet-shaped protrusion (42), which fits onto a ribbing or a pin on the tongue (49) and causes locking in place. In this way, for example the tongue (49) may be prevented from leaving the rivet-shaped protrusion (42) if there is no interference from outside.

The locking of the arm (30), shown in FIG. 16, into the rivet-shaped protrusion (42) can be taken from the enlargements of FIG. 16I (locked state) and FIG. 16E (unlocked state). The tongue (49) of the arm (30) engages in a toothing with a rack (53), which is provided in the rivet-shaped protrusion (42). This prevents the arm (30) from being released from the disc-shaped holding member (2) absent any external interference. At its lower end, i.e. at the end facing the first body (5), the rack (53) includes a pin (56) via which it is coupled to a handle member (54). The pin (56) serves as a point of contact for a force acting on the handle member (54). The toothing with the tongue (49) can be released by applying lateral pressure to the handle (54), so that the arm (30) can be released from the disk-shaped holding member (2). In some embodiments, the connection member (4) essentially consists of a pivotable arm (30) and a rivet-shaped protrusion (42), as e.g. shown in FIG. 16. As shown in FIG. 16, the connecting member (4) may consist solely of a pivotable arm (30) and a rivet-shaped protrusion (42).

A connection system according to the present disclosure may include a sterile barrier to prevent contamination prior to an, where applicable, during mounting. Such a sterile barrier may include or consist of a removable element sealing the interior space of a body. Such a sterile barrier may also include a non-removable element or may consist of a non-removable element sealing the interior space of a body. This may in particular serve in keeping the interior space of a fluid-carrying body sterile. In some embodiments, a removable barrier, such as a film, covers a port of an interior space of the first and/or second body. Such a barrier may be a protective film or a membrane, for example.

Figure 17B:
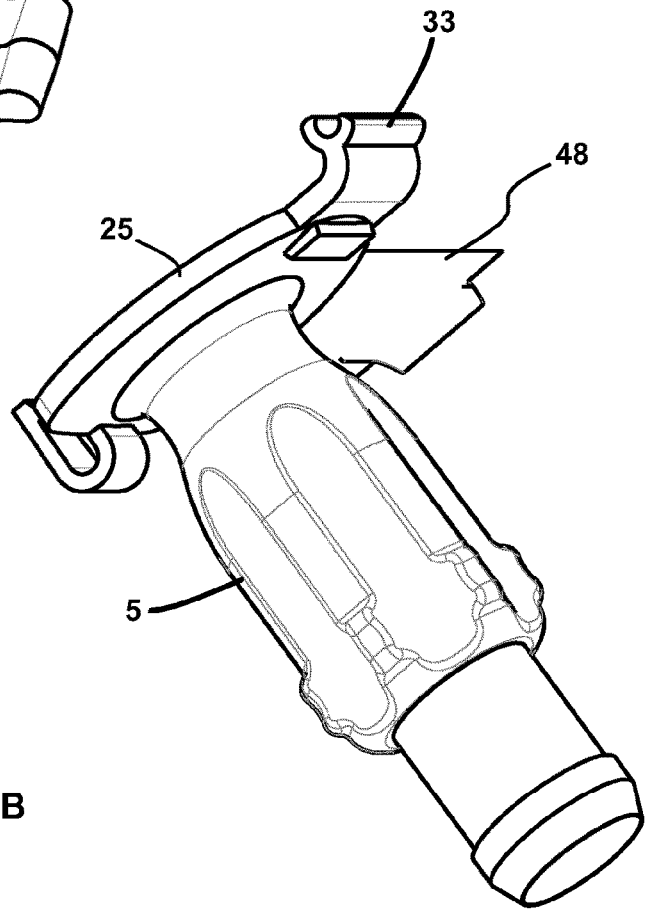
Figure 18E:
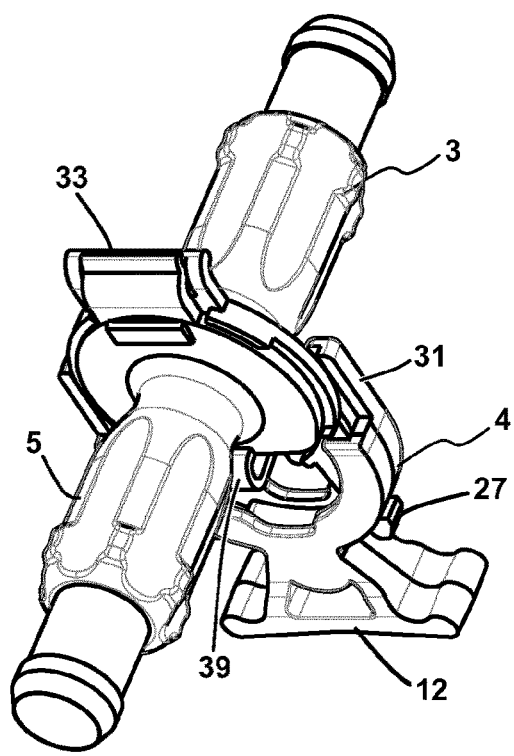
Figure 18F:
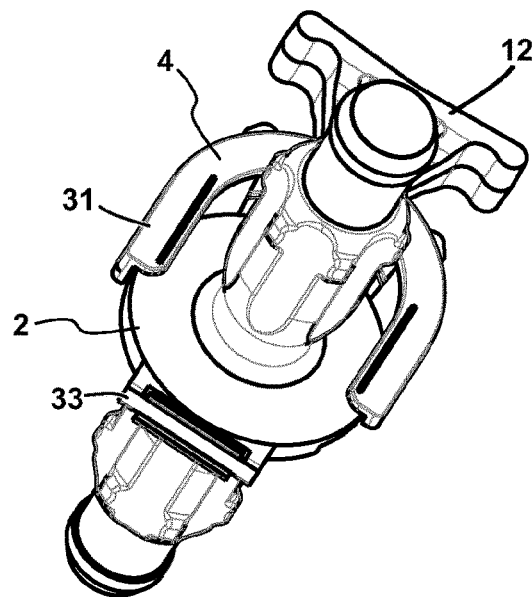
Figure 18G:
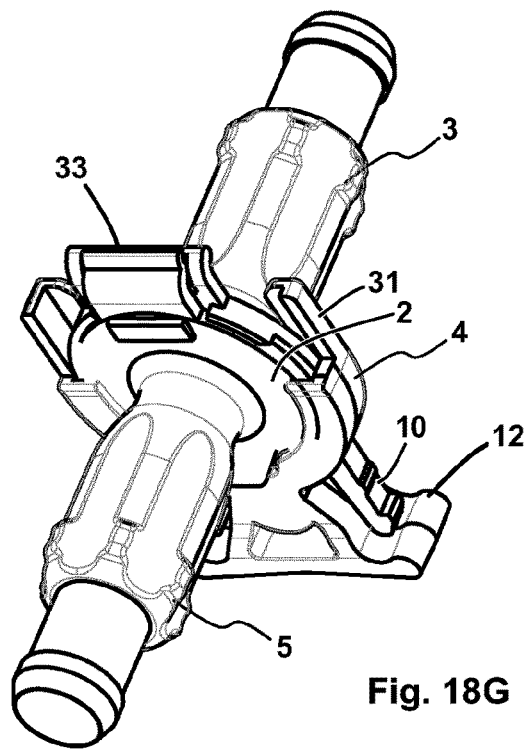
Figure 18H:
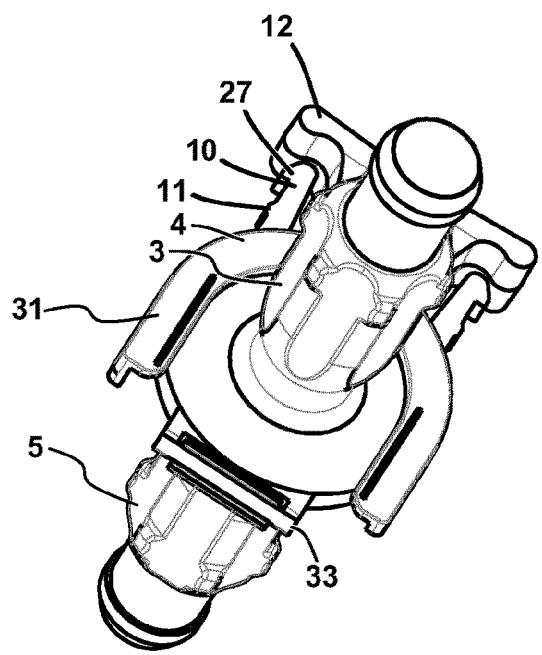

For example, a connection system for coupling two fluid-carrying bodies, as shown in FIGS. 17 and 18, may be equipped with a film. On an exemplary basis, FIGS. 17 and 18 show releasable protective films (48) adapted to isolate the interior space of the first and the second body from the ambience. A central opening (55) of the interior space of the second fluid-carrying body (3) is enclosed by a circumferential protrusion (46) in FIG. 17A. A releasable protective film (48) is in circumferential contact with this circumferential protrusion (46). If the first and the second body are, in this embodiment, being brought into a position in which the flange (25) of the first body and the flange-like disk-shaped holding member (2) of the second body butt against each other surface-to-surface by way of pivoting, see the hinge (33), the protective films (48) can be removed. In particular, after locking in place by the hook (39), a sterile connection of the interior spaces of the first and the second body can be ensured by the circumferential protrusion (46). The protective foils (48) can therefore be removed in such a connected position. FIGS. 18C to 18H show the connection system after removing the protective foils (48).

A device illustratively described herein may suitably be practiced and applied in the absence of any element or elements, limitation or limitations, not specifically disclosed herein. The terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the device disclosed herein has been described and illustrated in sufficient detail for those skilled in the art to utilize them, modification and variation of the embodiments disclosed herein may be resorted to by those skilled in the art, and that such modifications and variations are considered to be within the scope of this invention.

The contents of the articles, patents, and patent applications, and all other documents and electronically available information mentioned or cited herein, are hereby incorporated by reference in their entirety to the same extent as if each individual publication was specifically and individually indicated to be incorporated by reference. In case of conflict, the present document will control. Applicants reserve the right to physically incorporate into this document any, including all materials and information from any such articles, patents, patent applications, or other physical and/or electronic documents.

The listing or discussion of a previously published document in this specification should not necessarily be taken as an acknowledgement that the document is part of the state of the art or is common general knowledge.

It should be understood that the foregoing description is intended to illustrate and not to limit the scope of the invention, which is defined by the scope of the subsequent claims. Other embodiments are within the scope of the following claims.

The invention has been described broadly and generically herein. Each of the narrower species and subgeneric groupings falling within the generic disclosure also form part of the device. This includes the generic description of the device with a proviso or negative limitation removing any subject matter from the genus, regardless of whether or not the excised material is specifically recited herein.

Other embodiments are within the appending claims. Where features or aspects of the invention are given in terms of Markush groups, those skilled in the art will recognize that the invention is also thereby described in terms of any individual member or subgroup of members of the Markush group.

The invention claimed is:

1. A connection system for releasably force-fittingly coupling a first body (5) to a fluid-carrying system via a fluid-tight membrane (1),
    the connection system comprising the membrane (1) and a second body (3) having an interior space coupled to the fluid-carrying system, and the first body (5) comprising a first end with a flange (25),
    wherein the second body (3) comprises a second end with an interior space (23), a circumferential wall (22) and an opening (43), wherein the circumferential wall (22) comprises a membrane contact portion (9) circumferential around the opening (43), the membrane contact portion (9) being in contact with the membrane (1), wherein
        (a) the connection system comprises a disk-shaped holding member (2) with a passage (35), a first side, a second side and a peripheral outer edge (24), at least one of the first side and the passage (35) of the holding member (2) being coupled to the membrane (1), wherein the second side of the holding member (2) is designed for surface-to-surface contact with the flange (25) of the first body (5), and wherein the disk-shaped holding member (2) has a diameter that is larger than the height thereof, or
        (b) the second end of the second body (3) defines a flange-like disk-shaped holding member (2') having a peripheral outer edge (24), the flange-like disk-shaped holding member (2') being in contact with the membrane (1) and being designed for surface-to-surface contact with the flange (25) of the first body (5), and wherein the first body is fluid-carrying, and
    wherein the connection system comprises a releasable connection member (4), which is designed to at least partially grip around the peripheral outer edge (24) of the holding member (2, 2') and the flange (25) of the first body (5) circumferentially, such that the holding member (2, 2') is releasably force-fittingly fixable to the first body (5) by means of the connection member (4).

2. The connection system of claim 1, wherein the connection system comprises said disk-shaped holding member (2) with a passage (35), a first side, a second side and a peripheral outer edge (24), wherein
    on the first side of the holding member (2) there is arranged a circumferential wall (26), which is connected to the circumferential wall (22) of the second body (3).

3. The connection system of claim 1, wherein the disk-shaped holding member (2) and the connection member (4) lockably engage each other.

4. The connection system of claim 1, wherein
(a) the membrane contact portion (9) that is circumferential around the opening (43) is connected to the membrane (1); or
(b) at least one of the first side and the passage (35) of the disk-shaped holding member (2) is connected to the membrane (1).

5. The connection system of claim 1, wherein the first body (5) is a measuring element and the second body (3) is a measuring chamber connectable to a fluid system such that passage of fluid is allowed through the connection,
wherein the membrane (1) is substantially more flexible than the walls of the interior space of the second body (3) and allows a transmission of compressive forces from the measuring chamber to the measuring element (5),
wherein the first side and the passage (35) of the holding member (2) are in contact with the membrane (1),
wherein the first side of the holding member (2) is coupled to the membrane (1) and to the circumferential wall (22) of the measuring chamber (3), and the second side is adapted for surface-to-surface contact with the flange (25) of the measuring element (5).

6. The connection system of claim 1, wherein
(a) the membrane (1) is welded, glued or sealed to at least one of the circumferential wall (22) of the second body (3) and to the holding member (2), or the membrane (1) is clamped, connected or a combination thereof to the circumferential wall (22) wherein the membrane (1) is connected to the circumferential wall (22) by means of at least one of multi-component injection molding and liquid silicone rubber or by a combination thereof; or
(b) the holding member (2) is connected to the circumferential wall (22) of the second body by one of welding, gluing, sealing, clamping, multi-component injection molding, of liquid silicone rubber or by a combination of multi-component injection molding and liquid silicone rubber; or
(c) the holding member (2) is connected to the circumferential wall (22) of the second body by one of welding, gluing sealing, or clamping, and by means of one of multi-component injection molding, liquid silicone rubber or a combination thereof.

7. The connection system of claim 1, wherein
the holding member (2) comprises at least one arm (10) and wherein the connection member (4) comprises an essentially U-shaped clamp with two legs (31), and wherein the essentially U-shaped clamp comprises an opening or an outlet accommodating the arm (10), and/or
the connection member (4) comprises one or more clamping levers which are movably coupled to the holding member (2) and are adapted to at least partially grip around the flange (25) of the first body (5), or
the connection member (4) comprises an arm (30), the arm being movably coupled to the holding member (2) and adapted to grip around the outer side of the flange (25) of the first body (5) and the peripheral outer edge (24) of the holding member (2) or
the connection member (4) comprises a first thread and the holding member (2) comprises a second thread, wherein the first and the second thread fit into one another and are screwed together, or
the connection member (4) comprises a circumferential wall comprising the peripheral outer edge (24) of the holding member (2), the circumferential wall comprising a plurality of axially offset recesses, and wherein the peripheral outer edge (24) of the holding member (2) comprises a plurality of axially offset protrusions and wherein the plurality of axially offset protrusions are held in the plurality of offset recesses in the form of a bayonet closure.

8. The connection system of claim 1, wherein the second side of the holding member (2) comprises a peripheral hook element (7), the hook element (7) being adapted to at least partially grip around the outer side of the flange (25) of the first body (5).

9. The connection system of claim 1, wherein the connection member (4) comprises
one or more clamping levers and a holding member (2) with at least one hook element (7), or
one or more snap connections and a holding member (2) with one or more hook elements (7), or
two or more clamping levers, or
an essentially U-shaped clamp and a holding member (2) with one or more hook elements (7).

10. The connection system of claim 1, wherein the connection member (4) is defined by an essentially U-shaped clamp having an upper pair of legs, a lower pair of legs and a side wall (28) connecting each upper and lower leg, the side wall (28) comprising a recess (13) on the side of each leg,
the holding member (2) comprising a pair of arms (10) arranged parallel to the plane of the flange (25),
wherein the holding member (2) is arranged between the upper and the lower leg of the essentially U-shaped clamp (6) such that the ends of the arms (10) are insertable into the recess (13).

11. A connection system for releasably force-fittingly coupling the interior space of a first fluid-carrying body (5) to the interior space of a second fluid-carrying body (3),
wherein the first body (5) comprises a first end with a flange (25) and an outlet of the interior space of the first fluid-carrying body (5), and the second body (3) comprises a second end defining a flange-like disc-shaped holding member (2'), comprising a peripheral outer edge (24) and a central opening (55) of the interior space of the second fluid-carrying body (3),
the holding member (2') being coupled to the flange (25) of the first body (5), such that the holding member (2') can be seated on the flange (25) of the first body (5),
wherein the connection system comprises a connection member (4) which is designed to at least partially grip around the peripheral outer edge (24) of the holding member (2') and the flange (25) of the first body (5), such that the holding member (2') is force-fittingly fixed to the first body (5) by means of the releasable connection member (4),
wherein the holding member (2') comprises at least one arm (10), and wherein the connection member (4) comprises an essentially U-shaped clamp with two legs (31), and wherein the essentially U-shaped clamp comprises a recess (13), into which the arm (10) can be slid.

12. The connection system of claim 11, wherein the holding member (2) comprises a first side and a second side, the first side of the holding member (2) being in contact with the flange (25) of the first body (5), and wherein a circumferential protrusion (46) is arranged on the first side of the holding member (2).

13. The connection system of claim 11, further comprising a membrane (1) arranged between the flange (25) of the first body (5) and the first side of the holding member (2) of the second body (3).

14. The connection system of claim 11, wherein the first fluid-carrying body (5) and the second fluid-carrying body (3) are pivotally connected to each other.

15. The connection system of claim 11, wherein the second side of the holding member (2) comprises a peripheral hook element (7), the hook element (7) being adapted to at least partially grip around the outer side of the flange (25) of the first body (5).

16. The connection system of claim 11, wherein the connection member (4) comprises one or more clamping levers and a holding member (2) with at least one hook element (7), or one or more snap connections and a holding member (2) with one or more hook elements (7), or two or more clamping levers, or an essentially U-shaped clamp and a holding member (2) with one or more hook elements (7).

17. The connection system of claim 11, wherein the connection member (4) is defined by said essentially U-shaped clamp, the essentially U-shaped clamp having an upper pair of legs, a lower pair of legs and a side wall (28) connecting each upper and lower leg, the side wall (28) comprising a recess (13) on the side of each leg, the holding member (2) comprising a pair of arms (10) arranged parallel to the plane of the flange (25), wherein the holding member (2) is arranged between the upper and the lower leg of the essentially U-shaped clamp (6) such that the ends of the arms (10) are insertable into the recess (13).

18. A method of releasably force-fittingly coupling a first body (5) to a fluid-carrying system via a fluid-tight membrane (1), wherein the first body (5) comprises a first end with a flange (25), and wherein an interior space (23) of a second body (3) is coupled to the fluid-carrying system, wherein the second body (3) comprises a second end with a circumferential wall (22) as well as the interior space (23) with an opening (43) thereof, the circumferential wall (22) comprising a membrane contact portion (9) circumferential around the opening (43) and in contact with the membrane (1), wherein furthermore the second end of the second body (3) is in contact with a disk-shaped holding member (2), wherein the disc-shaped holding member (2) comprises a passage (35), a first side, a second side and a peripheral outer edge (24), the first side of the holding member (2) being in contact with the first end of the first body (5), and wherein at least one of the first side and the passage (35) of the disk-shaped holding member (2) is furthermore coupled to the membrane (1), and wherein the second side of the holding member (2) is designed for surface-to-surface contact with the flange (25) of the first body (5), the method comprising:

aligning and bringing into contact the disk-shaped holding member (2), being located at the second end of the second body (3), and the first end of the first body (5), such that the second side of the disk-shaped holding member (2) rests on the flange (25) of the first body (5), and thereafter arranging a releasable connection member (4) to at least partially grip around the flange (25) of the first body (5) and the peripheral outer edge (24) of the disk-shaped holding member, such that the holding member (2) is force-fittingly fixed to the first body (5) by means of the connection member (4).

\* \* \* \* \*